US006818627B1

(12) United States Patent
Mahalingam et al.

(10) Patent No.: US 6,818,627 B1
(45) Date of Patent: Nov. 16, 2004

(54) FUNCTIONAL FRAGMENTS OF HIV-1 VPR PROTEIN AND METHODS OF USING THE SAME

(75) Inventors: Sundarasamy Mahalingam, Birmingham, AL (US); Velpandi Ayyavoo, Monroeville, PA (US); Mamata Patel, Hoboken, NJ (US); Thomas Kieber-Emmons, Newtown Square, PA (US); David B. Weiner, Merion Station, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/485,421

(22) PCT Filed: Aug. 14, 1998

(86) PCT No.: PCT/US98/16890

§ 371 (c)(1),
(2), (4) Date: Oct. 5, 2000

(87) PCT Pub. No.: WO99/09412

PCT Pub. Date: Feb. 25, 1999

Related U.S. Application Data

(60) Provisional application No. 60/055,754, filed on Aug. 14, 1997.

(51) Int. Cl.[7] .................. A61K 48/00; A61K 38/00; C12P 21/06; C12N 15/74; C07H 21/04
(52) U.S. Cl. .................. 514/44; 435/69.1; 435/69.7; 435/320.1; 435/455; 530/350; 530/402; 536/23.1; 514/2
(58) Field of Search ............ 536/23.1, 24.1, 536/24.5; 435/7.1, 320.1, 69.1, 455, 69.7; 530/350; 514/44, 2

(56) References Cited

U.S. PATENT DOCUMENTS

| 4,235,871 | A | | 11/1980 | Papahadjopoulos et al. .. 424/19 |
|---|---|---|---|---|
| 4,241,046 | A | | 12/1980 | Papahadjopoulos et al. .. 424/19 |
| 4,394,448 | A | | 7/1983 | Szoka, Jr. et al. .......... 435/172 |
| 5,459,127 | A | | 10/1995 | Felgner et al. ................. 514/7 |
| 5,580,859 | A | | 12/1996 | Felgner et al. ................ 514/44 |
| 5,589,466 | A | | 12/1996 | Felgner et al. ................ 514/44 |
| 5,593,972 | A | | 1/1997 | Weiner et al. ................ 514/44 |
| 5,614,503 | A | | 3/1997 | Chaudhary et al. ........... 514/44 |
| 5,622,712 | A | | 4/1997 | Eppstein et al. ............. 424/450 |
| 5,639,598 | A | | 6/1997 | Weiner et al. ................. 435/5 |
| 5,676,954 | A | | 10/1997 | Brigham .................... 424/450 |
| 5,703,055 | A | | 12/1997 | Felgner et al. ................ 514/44 |
| 5,707,618 | A | | 1/1998 | Armentano et al. ..... 424/93.21 |
| 5,739,118 | A | | 4/1998 | Carrano et al. ............... 514/44 |
| 5,756,283 | A | | 5/1998 | Wilson et al. .................. 435/5 |
| 5,763,190 | A | | 6/1998 | Weiner et al. ............... 435/7.1 |
| 5,780,220 | A | | 7/1998 | Weiner et al. .................. 435/5 |
| 5,874,225 | A | | 2/1999 | Weiner et al. .............. 435/7.1 |
| 6,005,004 | A | * | 12/1999 | Katz et al. .................. 514/549 |
| 6,043,081 | A | * | 3/2000 | Cohen et al. ............ 435/320.1 |
| 6,232,295 | B1 | * | 5/2001 | Kayyem et al. ............... 514/44 |
| 6,468,986 | B1 | * | 10/2002 | Zuckermann et al. ......... 514/44 |

FOREIGN PATENT DOCUMENTS

| WO | WO 90/11092 | | 10/1990 |
|---|---|---|---|
| WO | WO 93/17706 | | 9/1993 |
| WO | WO 94/16737 | | 8/1994 |
| WO | WO 94/19456 | | 9/1994 |
| WO | WO 96/08970 | * | 9/1995 |
| WO | WO 96/08970 | | 3/1996 |
| WO | WO 96/10038 | | 4/1996 |

OTHER PUBLICATIONS

HIV vpr: NCBI database 2003.*
Di Marzio, et al., "Mutational Analysis of Cell Cycle Arrest, Nuclear Localization and Virion Packaging of Human Immunodeficiency Virus Type 1 Vpr." *Journal of Virology*, 1995, 69, 7909–7916.
Fisher et al., "A molecular clone of HTLV–III with biological activity." Nature, 1985, 316, 262–265.
Fletcher et al., "Nuclear import and cell cycle arrest functions of the HIV–1 Vpr protein are encoded by two separate genes in HIV–2/SIV$_{SM}$," *The EMBO Journal*, 1996, 15, 6155–6165.
He, et al., "Human Immunodeficiency Virus Type 1 Viral Protein R (Vpr) Arrests Cells in the $G_2$ Phase of the Cell Cycle by Inhibiting p34$^{cdc2}$ Activity," *Journal of Virology*, 1995, 6705–6711.
Heinzinger, et al., "The Vpr protein of human immunodeficiency virus type 1 influences nuclear localization of viral nucleic acids in nondividing host cells," *Proc. Natl. Acad. Sci. USA*. 1994, 91, 7311–7315.
Kneller, et al., "Improvements in Protein Secondary Structure Prediction by An Enhanced Neural Network." *J. Mol. Biol.*, 1990, 214, 717–182.
Lu, et al., "Human Immunodeficiency Virus Type 1 Viral Protein R Localization in Infected Cells and Virions." *Journal of Virology*, 1993, 67, 6542–6550.
Macreadie, et al., "A Domain of human immunodeficiency virus type 1 Vpr containing repeated H(S/F)RIG amino acid motifs causes cell growth arrest and structural defects" *Proc. Natl. Acad. Sci. USA*, 1995, 92, 2770–2774.

(List continued on next page.)

*Primary Examiner*—Janice Li
(74) *Attorney, Agent, or Firm*—Cozen O'Connor, P.C.

(57) ABSTRACT

Conjugated compositions comprising a fragment of HIV-1 Vpr or a non-HIV-1 Vpr protein conjugated to a therapeutic compound and methods of using the same to deliver therapeutic compounds to a cell's nucleus or for the preparation of drug delivery particles are disclosed. Functional fragments of HIV-1 Vpr and functional non-HIV-1 Vpr proteins, and pharmaceutical compositions comprising the same are disclosed. Methods of inhibiting cell proliferation and methods of treating an individual who has a hyperproliferative disease are disclosed. Methods of identifying compounds that inhibit Vpr protein binding to the p6 domain of p55 or to p6 protein and kits for performing such methods are disclosed.

20 Claims, 12 Drawing Sheets

OTHER PUBLICATIONS

Mahalingam, et al., "The Carboxy–Terminal Domain is Essential for Stability and Not for Virion Incorporation of HIV–1 Vpr into Virus Particles." *Virology*, 1995, 214,647–652.

Ratner, et al., "Complete nucleotide sequence of the AIDS virus, HTLV–III," *Nature*, 1985, 313, 277–284.

Ratner, et al., "Complete Nucleotide Sequences of Functional Clones of the AIDS Virus," *AIDS Research and Human Retroviruses*, 1987, 3, 57–69.

Refaeli, et al., "The glucocorticoid receptor type II complex is a target of the IIIV–1 vpr gene product." *Proc. Natl. Acad. Sci. USA*, 1995, 92, 3621–3625.

Starcich, et al., "Characterization of Long Terminal Repeat Sequences of HTLV–III." *Science*, 227, 538–540, 1985.

Yao, et al., "Mutagenic Analysis of Human Immunodeficiency Virus Type 1 Vpr: Role of a Predicted N–Terminal Alpha–Helical Structure in Vpr Nuclear Localization and Virion Incorporation," *Journal of Virology*, 1995, 69, 7032–7044.

Zhao, et al. "Biochemical Mechanism of HIV–1 Vpr Function," *J. of Biological Chemistry*, 1994, 269, 15577–15582.

U.S. patent application Ser. No. 08/167,608, Weiner, filed Dec. 15, 1993.

* cited by examiner-

```
HIV1-Vpr       1 M.....EQAP EDQGPQR.EY PNDWTLELLE ELKNEAVRHF PRIWLHSLGQ  44
HIV2/SIV-Vpr   1 M.....EERPP ENEGPQR.EP WDEWVVEVLE ELKEEALKHF DPRLLTALGN  45
HIV2/SIV-Vpx   1 MTNPRETIPP GNSGEETIEE AFDWLDRTVE AINREAVNHL PRELIFQVWQ   50

HIV-Vpr       45 HIYETYGDTW TGVEALIR..  ...ILQQLLF IHFRIGCRHS RIGIIQQRRT  89
HIV2/SIV-Vpr  46 HIYNRHGDTL EGAGELIR..  ...ILQRALF MHFRGGCIHS RIGQPGGGNP  90
HIV2/SIV-Vpx  51 RSWRYWHDEQ GMSRSYTKYR YLCLMQKAVF MHFKKGCTCR GEGHGPGGWR 100

HIV1-Vpr      90 RNGASKS....                                               96
HIV2/SIV-Vpr  91 LSAIPPSRSM L                                             101
HIV2/SIV-Vpx 101 SGPPPPPPG L                                              111
```

FIG. 1A

```
Vpr wt   MFQAPEDQGPQREPYNDWTLELLEELKNEAVRHFPRIWLHSLGQHIYETYGDTWTGVEALIRILQQLLFIHFRIGCRHSRIGIIQHRRTRNGASKS
E21.24P  ----------P-P--------------------------------------------------------------------------------
αL-A     -------------A-AA--A--------------------------------------------------------------------------
A30S     ------------------------------S----------------------------------------------------------------
A30L     ------------------------------L----------------------------------------------------------------
A59P     -----------------------------------------------------------P------------------------------------
L64S     ----------------------------------------------------------------S-------------------------------
L67S     -------------------------------------------------------------------S----------------------------
L68S     --------------------------------------------------------------------S---------------------------
H71C     -----------------------------------------------------------------------C------------------------
H71Y     -----------------------------------------------------------------------Y------------------------
G75A     ---------------------------------------------------------------------------A--------------------
C76S     ----------------------------------------------------------------------------S-------------------
HXB2     MEQAPEDQGPQREPYNDWTLELLEELKNEAVRHFPRIWLHSLGQHIYETYGDIWIGVEALIRILQQLLFIHFQNWVST
```

FIG. 1B

```
         MEQAPEDQGPQREYPNDWTLELLEELKNEAVRHFPRIWLHSLGQHIYETYGDTWTGVEALIRILQQLLFIHFRIGCRHSRIGIIQQRRTRNGASKS
vpr      ----------------------HHHHHHHHHHHHHEHH----EEEE-----HHHHHHHHHHHHHHHHHHHHHHHHHEHEE----E-EEE--------
vpr      ----------------------HHHHHHHHHHHHHEHH----EEEE-----HHHHHHHHHHHHHHHHHHHHHHHHHEHEE----E-EEE--------
E21,24P  ----------------------HHHHHHHHHHHHHHHHH---EEEE-----HHHHHHHHHHHHHHHHHHHHHHHHHEHEE----E-EEE--------
aL-A     ----------------------HHHHHHHHHHHH----HHEHH-EEEE----HHHHHHHHHHHHHHHHHHHHHHHHHEHEE----E-EEE--------
A30S     ----------------------HHHHHHHHHHHHHHHHHHH-EEEE-----HHHHHHHHHHHHHHHHHHHHHHHHHEHEE----E-EEE--------
A30L     ----------------------HHHHHHHHHHHHHHHHHH--EEEE-----HHHHHHHHHHHHHHHHHHHHHHHHHEHEE----E-EEE--------
A59P     ----------------------HHHHHHHHHHHHHHHHHH--EEEE------HHHHHHHHHHHHHHHHHHHHHHHHEHEE----E-EEE--------
L64S     ----------------------HHHHHHHHHHHHHHHHHH--EEEE-----HHHHHHHHHHHHHHHHHHHHHHHHEEEE-----E-EEE--------
L67S     ----------------------HHHHHHHHHHHHHHHHHH--EEEE-----HHHHHHHHHHHHHHHHHHHHHHHHEEEEE----E-EEE--------
L68S     ----------------------HHHHHHHHHHHHHHHHHH--EEEF-----HHHHHHHHHHHHHHHHHHHHHHHHEEHEE----E-EEE--------
H71C     ----------------------HHHHHHHHHHHHHHHHHH--EEEE-----HHHHHHHHHHHHHHHHHHHHHHHHHEEEE----E-EEE--------
H71Y     ----------------------HHHHHHHHHHHHHHHHHH--EEEE-----HHHHHHHHHHHHHHHHHHHHHHHHHEEEE----E-EEE--------
G75A     ----------------------HHHHHHHHHHHHHHHHHH--EEEE-----HHHHHHHHHHHHHHHHHHHHHHHHHHHHH------EEE--------
C76S     ----------------------HHHHHHHHHHHHHHHHHH--EEEE-----HHHHHHHHHHHHHHHHHHHHHHHHHEEHEE---EEEEE--------
```

FIG.1D

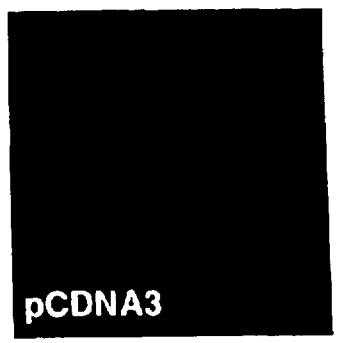
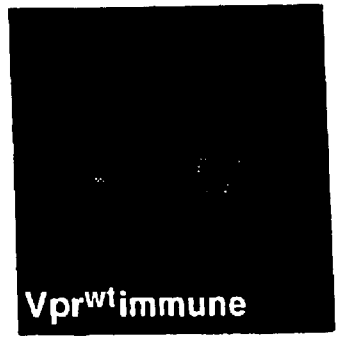
FIG.3A  FIG.3B  FIG.3C
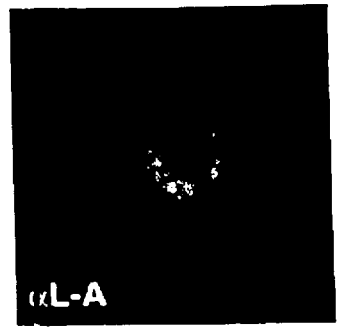
FIG.3D  FIG.3E  FIG.3F
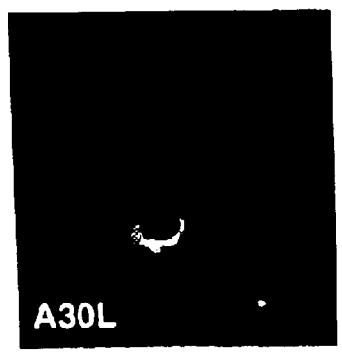
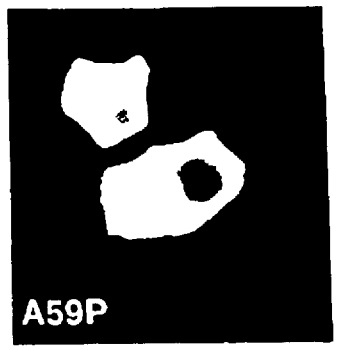
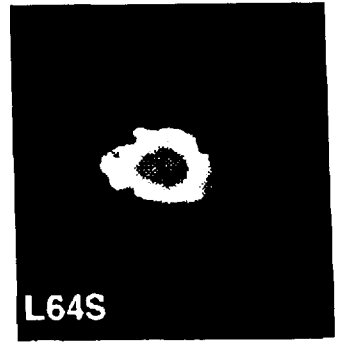
FIG.3G  FIG.3H  FIG.3I

FIG.3J  FIG.3K  FIG.3L
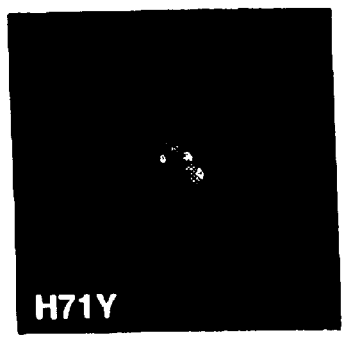
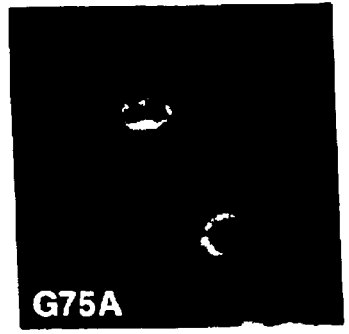
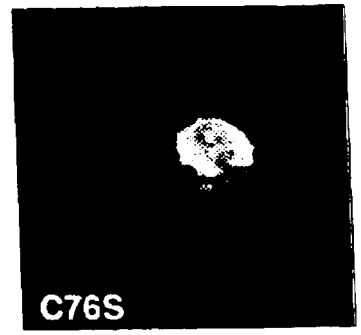
FIG.3M  FIG.3N  FIG.3O

FUNCTIONAL FRAGMENTS OF HIV-1 VPR PROTEIN AND METHODS OF USING THE SAME

CROSS REFERENCE TO RELATED APPLICATIONS

This application claims priority to U.S. Provisional Application Ser. Number 60/055,754, filed on Aug. 14, 1997 which is incorporated herein be reference.

FIELD OF THE INVENTION

The present invention relates to fragments of HIV-1 Vpr protein which function in nuclear localization, virion packaging, cell cycle arrest and/or cell differentiation. The present invention relates to non-Vpr proteins which comprise such fragments of HIV-1 Vpr protein. The present invention also relates to methods of using such fragments and proteins to localize proteins to a cell's nucleus, in assays to identify compounds which inhibit virion packaging, to method of arresting the cell cycle and to methods of inducing cell differentiation.

BACKGROUND OF THE INVENTION

The present invention is related to U.S. Ser. No. 08/019,601 filed Feb. 19, 1993, issued as U.S. Pat. No. 5,874,225; U.S. Ser. No. 08/167,608 filed Dec. 15, 1993, now allowed; U.S. Ser. No. 08/246,177 filed May 19, 1994, issued as U.S. Pat. No. 5,639,598; U.S. Ser. No. 08/309,644 filed Sep. 21, 1994, issued as U.S. Pat. No. 5,763,190 on Jun. 9, 1998; U.S. Ser. No. 08/809,186 filed Feb. 3, 1995, issued as U.S. Pat. No. 5,780,220; U.S. Ser. No. 08/505,196 filed Oct. 11, 1995, now abandoned; and U.S. Ser. No. 08/809,186 filed Mar. 20, 1997, issued as U.S. Pat. No. 6,667,157; which are each incorporated herein by reference.

The human immunodeficiency virus type 1 (HIV-1) accessory gene vpr, while dispensable for viral replication in T-cell lines and activated primary peripheral blood mononuclear cells (PBMC), is required for efficient replication in primary monocyte/macrophages.

The Vpr protein has been characterized as an oligomer. HIV-2 and SIV code for a second protein, Vpx, which shares considerable sequence homology with. Both proteins are packaged efficiently in HIV and SIV viral particles. Virion localization studies place both Vpr and Vpx outside the core structure. Although Vpr and Vpx are not part of the Gag structural polyprotein, their incorporation requires an anchor to associate with the assembling capsid structures. The C-terminal portion of the Gag precursor corresponding to the p6 protein appears to constitute such an anchor through an unknown mechanism. In addition, p6 is essential for the incorporation of both Vpr and Vpx into virus particles. A predicted putative α-helical domain near the amino terminus plays an important role in the packaging of Vpr into virions and in maintaining protein stability.

Several possible roles have been suggested for Vpr in HWV-1 replication. Vpr can modestly transactivate HIV-1 LTR and thus may upregulate viral gene expression in newly infected cells before the appearance of Tat. It has been found to enhance the nuclear migration of the preintegration complex in newly infected nondividing cells. Significantly, Vpr induces cellular differentiation which includes the activation of specific host cell gene transcription and growth arrest in several tumor cell lines, even in the absence of any other viral proteins. This suggests that Vpr, itself, may be sufficient to alter cellular functions. Vpr has been reported to block cell cycling in G2/M phase of the cell cycles. This finding has been associated with a change in the phosphorylation state of CDC2 kinase. Furthermore, Vpr expression appears to inhibit the establishment of chronic infection. Vpr has been reported to causes growth arrest and structural defects in yeast. Functional studies have shown that Vpr accelerates HIV-1 replication in some T-lymphoid cells lines in primary macrophages where the effects of Vpr are more pronounced.

It has also been reported that Vpr has transcellular activity. Both Vpr purified from plasma of HIV-1 seropositive individuals and purified recombinant Vpr, were capable of inducing latent cells into high-level viral producer when added to culture media at low concentrations. Mechanistically, it is conceivable that this transcellular activity is mediated by the same mechanisms which modify cellular growth and differentiation. It has been reported that Vpr is primarily localized in the nucleus when expressed in the absence of other HIV-1 proteins. Although, no classical nuclear localization signal has been clearly identified for Vpr, it has been suggested that Vpr may gain access to the nucleus by specific interactions with nuclear proteins. In this regard, proteins that interact with Vpr in host cells have been reported but not molecularly cloned. Interestingly, one of these Vpr targets, designated Vpr-interacting protein, or RIP-1, appears to be translocated to the nucleus following its interaction with Vpr or triggering by glucocorticoid receptor (GR) ligands, supporting a possible role for the GR pathway in Vpr function.

The molecular relationship between these different functions of Vpr have not yet been defined. There is a need to identify the functional activity of the various domains of Vpr protein.

SUMMARY OF THE INVENTION

The present invention relates to conjugated compositions comprising a fragment of HTV-1 Vpr comprising amino acid sequence 17–36 and/or 59–84 or a non-HIV-1 Vpr protein comprising amino acids amino acids 17–36 and 59–84 conjugated to a therapeutic compound.

The present invention further relates to methods of delivering a therapeutic compound to the nucleus of a cell. The method comprises the step of contacting the cell with a conjugated compound that is either the therapeutic compound conjugated to a fragment of HIV-1 Vpr protein comprising amino acids 17–36 and/or 59–84 or the therapeutic compound conjugated to a non-HIV-1 Vpr protein comprising amino acids 17–36 and/or 59–84 of HIV-1 Vpr protein. The conjugated compound is taken up by said cell and localized to the nucleus of the cell.

The present invention further relates to fragments of HIV-1 Vpr comprising amino acid sequences 17–36 and/or 59–84 and to non-HIV-1 Vpr proteins comprising amino acids 17–36 and/or 59–84 of HIV-1 Vpr protein.

The present invention further relates to methods of inhibiting cell proliferation. The methods comprise the step of arresting said cell's advance in the cell cycle by contacting said cell with a fragment of HIV-1 Vpr protein comprising amino acids 19–35 and/or 74–89; or a non-HIV-1 Vpr protein comprising amino acids 19–35 and/or 74–89 of HIV-1 Vpr protein; or a nucleic acid molecule that encodes a fragment of HIV-1 Vpr protein comprising amino acids 19–35 and/or 74–89; or a nucleic acid molecule that encodes a non-HIV-1 Vpr protein comprising amino acids 19–35 and/or 74–89 of HIV-1 Vpr protein. The fragment of HIV-1 Vpr or non-HIV-1 Vpr protein is taken up by said cell or the nucleic acid molecule that encodes a fragment of HIV-1 Vpr protein or the nucleic acid molecule that encodes the non-HIV-1 Vpr protein is taken up by the cell and expressed to produce the fragment of HIV-1 Vpr or non-HIV-1 Vpr protein in the cell. The fragment of HIV-1 Vpr or non-HIV-1 Vpr protein inhibits said cell from advancing in said cell cycle.

The present invention further relates to methods of treating an individual who has a hyperproliferative disease. The method comprises the step of administering to the individual in an amount effective to inhibit cell proliferation a composition comprising: a fragment of HIV-1 Vpr protein comprising amino acids 19–35 and/or 74–89; or a non-HIV-1 Vpr protein comprising amino acids 19–35 and/or 74–89 of HIV-1 Vpr protein; or a nucleic acid molecule that encodes a fragment of HIV-1 Vpr protein comprising amino acids 19–35 and/or 74–89; or a nucleic acid molecule that encodes a non-HIV-1 Vpr protein comprising amino acids 19–35 and/or 74–89 of HIV-1 Vpr protein. The fragment of HIV-1 Vpr or non-HIV-1 Vpr protein molecule is taken up by proliferating cells of the individual or the nucleic acid molecule that encodes a fragment of HIV-1 Vpr protein or the nucleic acid molecule that encodes the non-HIV-1 Vpr protein is taken up by a proliferating cell of the individual and expressed to produce the fragment of HIV-1 Vpr or non-HIV-1 Vpr protein molecule in the cell. The fragment of HIV-1 Vpr or non-HIV-1 Vpr protein molecule inhibit the cell from advancing in the cell cycle.

The present invention further relates to a fragment of HIV-Vpr comprising amino acid sequence or a non-HIV-1 Vpr protein comprising amino acids 19–35 and/or 74–89 of HIV-1 Vpr protein.

The present invention further relates to pharmaceutical composition comprising a fragment of HIV-Vpr comprising amino acid sequence or a non-HIV-1 Vpr protein comprising amino acids 19–35 and/or 74–81of HIV-1 Vpr protein and a pharmaceutically acceptable carrier.

The present invention further relates to a nucleic acid molecule that encodes a fragment of HIV-1 Vpr protein comprising amino acids 19–35 and/or 74–89; or a nucleic acid molecule that encodes a non-HIV-1 Vpr protein comprising amino acids 19–35 and/or 74–89 of HIV-1 Vpr protein; and to pharmaceutical compositions comprising the same.

The present invention further relates to methods of identifying compounds that inhibit Vpr protein binding to the p6 domain of p55 or to p6 protein. The methods comprise the steps of contacting a fragment of HIV-1 Vpr comprising amino acid sequence 17–36 or a non-HIV-1 Vpr protein comprising amino acids 17–36 of HIV-1 Vpr protein with a protein comprising an HIV-1 Gag protein p6 domain in the presence of a test compound. The level of binding between the fragment of HIV-1 Vpr or the non-HIV-1 Vpr protein and the protein comprising an HIV-1 Gag p6 domain is determined and compared to the level of binding between the fragment of HIV-1 Vpr or the non-HIV-1 Vpr protein and the protein comprising an HIV-1 Gag p6 domain contacted in the absence of a test compound.

The present invention further relates to kits for identifying compounds which inhibit Vpr protein binding to p55's p6 domain or to p6 protein. The kits comprise a first container comprising a fragment of HIV-1 Vpr comprising amino acid sequence 17–36 or a non-HIV-1 Vpr protein comprising amino acids 17–36 of HIV-1 Vpr protein; and a second container comprising a protein comprising an HIV-1 Gag protein p6 domain.

The present invention further relates to fusion proteins comprising Vpr amino acid sequence 17–36 and non-Vpr amino acid sequences, and drug delivery particles comprising the same.

BRIEF DESCRIPTION OF THE FIGURES

FIGS. 1A–1D show construction and expression of mutant Vpr molecules. FIG. 1A shows an amino acid sequence comparison of Vpr of HIV-1 (SEQ ID NO: 1) and 2/SIV (SEQ ID NO.2) and Vpx HIV-2/SIV (SEQ ID NO:3). Numbers denote positions of amino acid residues for each protein sequence provided. FIG. 1B shows expression plasmids for the synthesis of mutant Vpr molecules were generated by overlap Polymerase Chain Reaction (PCR) at the indicated codons. PCR-amplified mutant vpr gene fragments were digested with HindIII and XhoI and ligated to pCDNA3 vector to produce Vpr mutant expression plasmids. VPR wt is SEQ ID NO:4; E21,24P is SEQ ID NO:5; αL-A is SEQ ID NO:6; A30S is SEQ ID NO:7; A30L is SEQ ID NO:8; A59P is SEQ ID NO:9; L64S is SEQ ID NO:10; L67S is SEQ ID NO:11; L68S is SEQ ID NO:12; H71C is SEQ ID NO:13; H71Y is SEQ ID NO:14; G75A is SEQ ID NO:15; C76S is SEQ ID NO:16; and HXB2 is SEQ ID NO:17. FIG. 1C shows recombinant vaccinia virus (vTF7-3) infected HeLa cells were transfected with wild type and mutant vpr expression plasmids. Transfected cells were labeled with $S_{35}$ protein labeling mix for 2 hours and the cell-associated Vpr proteins were immunoprecipitated with anti-Vpr antiserum as described in Materials and Methods. Immunoprecipitates were analyzed by SDS-12% PAGE. The designation of the Vpr plasmids is indicated at the top. FIG. 1D shows the secondary structure of Vpr (SEQ ID NO:18) was calculated using the program nnpredict (Kneller, D. G. et al., *J. Mol. Biol.*, 1990, 214: 171–182.). nnpredict is a program that predicts the secondary structure type for each residue in an amino acid sequence based on the prediction of a two-layer, feed-forward neural network. H is helical, E is extended and dash (–) is undefined, αL-A, L64S, and H71C display the same secondary profile as the Vpr wild-type, suggesting the importance of the Leu residues on the hydrophobic face and His in the C-terminus. Introduction of proline-residue in E21, E24 and A59 disrupt the respective helical domains.

FIGS. 3A–3O shows subcellular localization of wild type Vpr and the effect of substitutions at the different structural domains of Vpr. HeLa cells were infected with recombinant vaccinia virus vTF7-3 and transfected with Vpr expression plasmids. After overnight transfection the cells were fixed and stained with anti-Vpr serum followed by affinity-purified FITC-conjugated goat anti-rabbit IgG.

FIGS. 4A-1—4A-4, 4B-1–4B-2 and 4C show expression of HIV-1 Vpr independent of other viral genes inhibits cell proliferation. RD cells expressing Vpr arrest in cell cycle with 4N DNA content. FIGS. 4A-1–4A-4 shows flow cytometric analysis of RD cells stained with propidium iodide (PI). RD cells were transfected with vector alone, Vpr wt, Vpr mutants. FIGS. 4B-1–4B-2 shows morphology of RD cells expressing Vpr. RD cells were transfected with vector alone (a), and Vpr wt (b), After two days the cells were maintained in DMEM containing 2μm/ml puromycin. The cells were photographed 5 to 6 days later. FIG. 4C shows cell cycle arrest activity of Vpr mutants.

FIG. 6A represents a scheme for the incorporation of Vpr into virus particles through infraction with structural polyprotein p55Gag. FIG. 6B represents Vpr's nuclear localization and cell cycle arrest functions which were mediated by its interactions with cellular cofactor(s).

DESCRIPTION OF PREFERRED EMBODIMENTS OF THE INVENTION

Figure 1C:
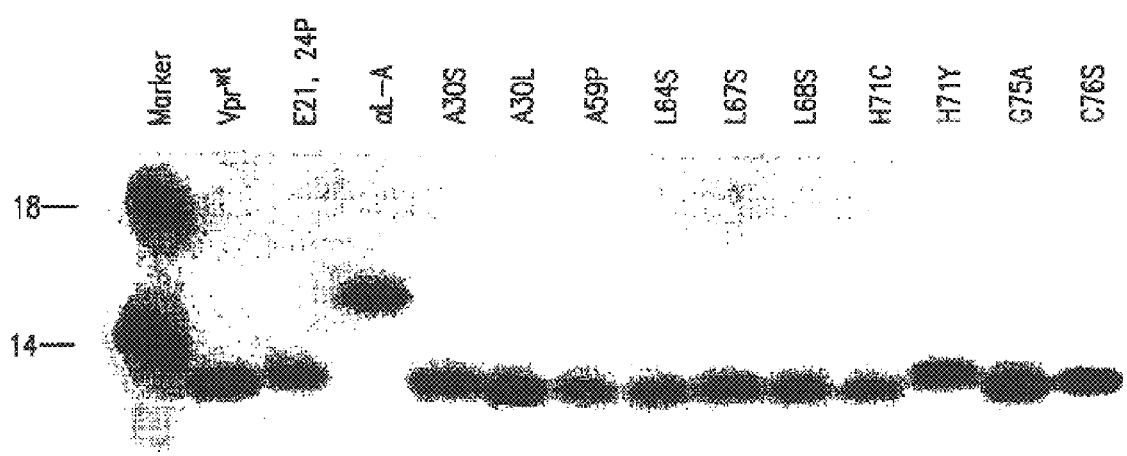

As used herein, the terms "fragment of HIV-1 Vpr protein" and "fragment of Vpr protein" are meant to refer to proteins which are not complete HIV-1 Vpr proteins (i.e. full length Vpr protein) but truncated forms which consist of contiguous amino acid sequences identical to contiguous amino acid sequences of portions of HIV-1 Vpr protein. A fragment of Vpr protein may be similar to full length Vpr protein. For example, a protein having amino acids 1–95 of Vpr protein but which is missing amino acid 96 is not identical a full length Vpr protein but is a fragment of Vpr protein.

In some embodiments, fragments of Vpr are less than 50 amino acids. In some embodiments, fragments of Vpr are less than 25 amino acids. In some embodiments, fragments of Vpr arc less than 20 amino acids. In some embodiments, fragments of Vpr are less than 15 amino acids. In some embodiments, fragments of Vpr are less than 13 amino acids. In some embodiments, fragments of Vpr are less than 10 amino acids. In sonic embodiments, fragments of Vpr are less than 8 amino acids. In some embodiments, fragments of Vpr are less than 5 amino acids. In sonic embodiments, fragment of Vpr are less than 4 amino acids.

As used herein, the term "hyperproliferative diseases" is meant to refer to those diseases and disorder characterized by hyperproliferation of cells. Examples of hyperproliferative diseases include all forms of cancer and psoriasis.

The term "pharmaceutical" is well known and widely understood by those skilled in the art. As used herein, the terms "pharmaceutical compositions" and "injectable pharmaceutical compositions" are meant to have their ordinary meaning as understood by those skilled in the art. Pharmaceutical compositions are required to meet specific standards regarding sterility, pyrogens, particulate matter as well as isotonicity and pH.

The present invention arises out of the discovery of functions and activities of the specific domains of the HIV-1 Vpr protein. It has been discovered that the domain characterized by amino acids 19–35 and 74–89 of Vpr protein is responsible for Vpr protein's ability to arrest a cell in the cell cycle. It has been discovered that the domain characterized by amino acids 17–36 of Vpr protein is responsible for Vpr protein's ability to interact with the p6 domain of the p55 Gag translation product. Such interaction is involved in the packaging of Vpr into HIV-1 particles. It has been discovered that the domain characterized by amino acids 17–36 and 59–84 of Vpr protein is responsible for Vpr protein's ability to localize into the nucleus of cells. These activities and functions of specific domains of Vpr protein allow for the use of fragments of Vpr protein and non-Vpr proteins which have a sequence of a fragment of Vpr protein, as well as nucleic acid molecules that encode such fragments of Vpr protein and non-Vpr proteins. Such proteinaceous and nucleic acid molecules may be used in methods of inhibit cell proliferation, including inhibiting cell proliferation of cancer cells, in methods of delivering conjugated compounds to the nucleus of cells, to methods of identifying compounds that inhibit HIV-1 viral particle assembly, and in methods of preparing and delivering fusion proteins to cells. The present invention provides pharmaceutical compositions comprising such proteinaceous and nucleic acid molecules also.

Several aspects of the invention relate to the discovery of the domain of Vpr protein responsible for the activity in which the cell's advance through the cell cycle is arrested. The ability to arrest the cell in the cell cycle allows for the inhibition of cell proliferation since the cell must pass through the cell cycle to complete cell division and thus proliferate. Fragments of Vpr protein which comprise amino acids 19–35 and/or 74–89 may be used to arrest a cell in the cell cycle and thus inhibit cell proliferation. Similarly, non-Vpr proteins which have a sequence of a fragment of Vpr protein which consist of amino acids 19–35 and/or 74–89 of Vpr protein may be used to arrest a cell in the cell cycle and thus inhibit cell proliferation. Likewise a nucleic acid molecule that encodes a fragment of Vpr protein which comprise amino acids 19–35 and/or 74–89 may be used to arrest a cell in the cell cycle and thus inhibit cell proliferation as can a nucleic acid molecule that encodes a non-Vpr protein which has a sequence of a fragment of Vpr protein which comprise amino acids 19–35 and/or 74–89. In some embodiments, pharmaceutical compositions are provided which comprise a pharmaceutically acceptable carrier and either: a fragment of Vpr protein which comprise amino acids 19–35 and/or 74–89; a non-Vpr protein which has a sequence of a fragment of Vpr protein which comprises amino acids 19–35 and/or 74–89; a nucleic acid molecule that encodes a fragment of Vpr protein which comprises amino acids 19–35 and/or 74–89: or a nucleic acid molecule that encodes a non-Vpr protein which has a sequence of a fragment of Vpr protein which comprises amino acids 19–35 and/or 74–89. Pharmaceutical compositions according to this aspect of the invention may be used to treat individuals suffering from diseases associated with hyperproliferating cells such as cancer or psoriasis. Pharmaceutical compositions of the present invention are particularly useful for treating cancer characterized by solid tumors. Accordingly, the present invention provides a method of treating an individual suffering from a disease associated with hyperproliferating cells which comprises the step of administering to said individual an amount of a pharmaceutical composition which comprise a pharmaceutically acceptable carrier and either: a fragment of Vpr protein which comprises amino acids 19–35 and/or 74–89 of Vpr protein; a non-Vpr protein which has a sequence of a fragment of Vpr protein which comprises amino acids 19–35 and/or 74–89; a nucleic acid molecule that encodes a fragment of Vpr protein which comprises amino acids 19–35 and/or 74–89; or a nucleic acid molecule that encodes a non-Vpr protein which has a sequence of a fragment of Vpr protein which comprises amino acids 19–35 and/or 74–89 of Vpr protein. The protein or nucleic acid is taken up by the cell. The protein causes the cell to cease advancing through the cell cycle. The nucleotide sequence of the nucleic acid molecule that encodes the fragment of Vpr or non-Vpr protein is expressed and the resulting translation product causes the cell to cease advancing through the cell cycle. The interruption in the cell cycle results in a discontinuation of cell division and proliferation. When an individual who has hyperproliferating cells is treated according to the methods of the invention, the hyperproliferating cells are arrested and stop dividing. Thus, for example, tumor growth is halted or slowed.

Fragments of Vpr protein and non-Vpr proteins which have a sequence of a fragment of Vpr protein comprising a fragment of Vpr protein may be produced by routine means using readily available starting materials as described above. The nucleic acid sequence encoding Vpr protein as well as the amino acid sequence of the protein are well known. The entire HIV genome is published. The lone terminal repeat sequences are reported in Stacich. B. et al., (1985) *Science* 227:538–540. Complete nucleotide sequences are reported in Ratner, L. et al., (1985) *Science* 313:277–284 and Ratner, L. et al., (1987) *AIDS Res. Hum. Retroviruses* 3:57–69. The DNA sequence of HIV-1/3B is published in Fisher, A., 1985 *Nature* 316:262,. The HIV-1 HXB2 strain nucleotide sequence is available on line from Genbank accession number K03455. The HIV DNA sequence is published in Reiz, M. S., 1992 *AIDS Res. Human Retro.* 8:1549. The sequence is accessible from Genbank No.: M17449. Each of these references including the publicly available sequence information are incorporated herein by reference.

DNA molecules that encode Vpr protein are readily available to the public. Plasmid pNL-43 which contains a DNA sequence encoding HIV-1 strain MN including the Vpr protein and plasmid pHXB2 which contains a DNA sequence encoding HIV strain HIV-1/3B are both available from AIDS Research Reference and Reagent Program (ARRRP). Division of AIDS, NIAID, NIH, Bethesda. Md.

Provision of a suitable DNA sequence encoding a desired protein permits the production of the protein using recombinant techniques now known in the art. The coding sequence can be obtained by retrieving the DNA sequence from the publicly available plasmids which comprise DNA encoding a fragment of Vpr protein or a non-Vpr protein that has a sequence of a fragment of Vpr protein. The DNA sequence may also be obtained from other sources of HIV DNA or can be prepared chemically using a synthesized nucleotide sequence. When the coding DNA is prepared synthetically, advantage can be taken of known codon preferences of the intended host where the DNA is to be expressed.

One having ordinary skill in the art can, using well known techniques, obtain a DNA molecule encoding Vpr protein and modify it, or synthesize a DNA molecule, to encode a fragment of Vpr protein or a non-Vpr protein that has a sequence of a fragment of Vpr protein. The DNA molecule can be inserted into a commercially available expression vector for use in well known expression systems. For example, the commercially available plasmid pSE420 (Invitrogen, San Diego, Calif.) may be used for production in *E. coli*. The commercially available plasmid pYES2 (Invitrogen, San Diego, Calif.) may be used for production in *S. cerevisiae* strains of yeast. The commercially available MaxBac™ (Invitrogen, San Diego. Calif.) complete baculovirus expression system may be used for production in insect cells. The commercially available plasmid pcDNA I (Invitrogen, San Diego, Calif.) may be used for production in may be used for production in mammalian cells such as Chinese Hamster Ovary cells.

One having ordinary skill in the art can use these commercial expression vectors systems or others to produce a fragment of Vpr protein or a non-Vpr protein that has a sequence of a fragment of Vpr protein using routine techniques and readily available starting materials.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989). Thus, the desired proteins can be prepared in both prokaryotic and eukaryotic systems, resulting in a spectrum of processed forms of the protein.

The most commonly used prokaryotic system remains *E. coli*, although other systems such as *B. subtilis* and Pseudomonas are also useful. Suitable control sequences for prokaryotic systems include both constitutive and inducible promoters including the lac promoter, the trp promoter, hybrid promoters such as tac promoter, the lambda phage P1 promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in prokaryotic hosts in this matter, the signal sequence is removed upon secretion.

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, as e.g. the baculovirus polyhedron promoter. As above, promoters can be either constitutive or inducible. For example, in mammalian systems, the mouse metallothionene promoter can be induced by the addition of heavy metal ions.

The particulars for the construction of expression systems suitable for desired hosts are known to those in the art. For recombinant production of the protein, the DNA encoding it is suitably ligated into the expression vector of choice and then used to transform the compatible host which is then cultured and maintained under conditions wherein expression of the foreign gene takes place. The protein of the present invention thus produced is recovered from the culture, either by lysing the cells or from the culture medium as appropriate and known to those in the art.

One having ordinary skill in the art can, using well known techniques, isolate the fragments of Vpr protein or the non-Vpr proteins which comprise a fragment of Vpr protein produced using such expression systems.

In addition to producing these proteins by recombinant techniques, automated amino acid synthesizers may also be employed to produce a fragment of Vpr protein or a non-Vpr protein that has a sequence of a fragment of Vpr protein. It should be further noted that if the proteins herein are made synthetically, substitution by amino acids which are not encoded by the gene may also be made. Alternative residues include, for example, the ω amino acids of the formula $H_2N(CH_2)_nCOOH$ wherein n is 2–6. These are neutral, nonpolar amino acids, as are sarcosine (Sar), t-butylalanine (t-BuAla). t-butylglycine (t-BuGly), N-methyl isoleucine (N-MeIle), and norleucine (Nleu). Phenylglycine, for example, can be substituted for Trp, Tyr or Phe, an aromatic neutral amino acid; citrulline (Cit) and methionine sulfoxide (MSO) are polar but neutral, cyclohexyl alanine (Cha) is neutral and nonpolar, cysteic acid (Cya) is acidic, and ornithine (Orn) is basic. The conformation conferring properties of the proline residues may be obtained if one or more of these is substituted by hydroxyproline (Hyp).

The pharmaceutical composition comprising a pharmaceutically acceptable carrier/diluent and a fragment of Vpr protein comprising amino acids 19–35 and 74–89 of HIV-1 Vpr protein or a non-Vpr protein that has a sequence of a fragment of Vpr protein comprising amino acids 19–35 and 74–89 of HIV-1 Vpr protein may be formulated by one having ordinary skill in the art with compositions selected depending upon the chosen mode of administration. Suitable pharmaceutical carriers are described in the most recent edition of *Remington's Pharmaceutical Sciences*, A. Osol, a standard reference text in this field.

For parenteral administration, the fragment of Vpr protein or non-Vpr protein that has a sequence of a fragment of Vpr protein can be, for example, formulated as a solution, suspension, emulsion or lyophilized powder in association with a pharmaceutically acceptable parenteral vehicle. Examples of such vehicles are water, saline, Rinser's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as a single doses or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

The pharmaceutical compositions comprising the fragment of Vpr protein or non-Vpr protein that has a sequence of a fragment of Vpr protein may be administered by any means that enables the active agent to reach the agent's site of action in the body of a mammal. Because proteins are subject to being digested when administered orally, parenteral administration, i.e., intravenous, subcutaneous, intramuscular, would ordinarily be used to optimize absorption. In addition, the pharmaceutical compositions of the present invention may be injected at a site at or near hyperproliferative growth. For example, administration may be by direct injection into a solid tumor mass or in the tissue directly adjacent thereto. If the individual to be treated is suffering from psoriasis, the fragment of Vpr protein or non-Vpr protein that has a sequence of a fragment of Vpr protein may be formulated with a pharmaceutically acceptable topical carrier and the formulation may be administered topically as a creme, lotion or ointment for example.

The dosage administered varies depending upon factors such as: pharmacodynamic characteristics; its mode and route of administration; age, health, and weight of the recipient; nature and extent of symptoms; kind of concurrent treatment; and frequency of treatment. Usually, a daily dosage of a fragment of Vpr protein or a non-Vpr protein that has a sequence of a fragment of Vpr protein can be about 1 μg to 100 milligrams per kilogram of body weight. Ordinarily 0.5 to 50, and preferably 1 to 10 milligrams per kilogram per day given in divided doses 1 to 6 times a day or in sustained release form is effective to obtain desired results.

Another aspect of the present invention relates to pharmaceutical compositions that comprise a pharmaceutically acceptable carrier/diluent and a nucleic acid molecule that encodes a fragment of Vpr protein or a non-Vpr protein that has a sequence of a fragment of Vpr protein. According to the present invention, genetic material that encodes a fragment of Vpr protein or a non-Vpr protein that has a sequence of a fragment of Vpr protein is delivered to an individual in an expressible form. The genetic material, DNA or RNA, is taken up by the cells of the individual and expressed. The fragment of Vpr protein or non-Vpr protein that has a sequence of a fragment of Vpr protein that is thereby produced can arrest hyperproliferating cells in the cell cycle, preventing them from advancing therethrough and thus inhibit cell division and ultimately cell proliferation. Thus, pharmaceutical compositions comprising genetic material that encodes a fragment of Vpr protein or a non-Vpr protein that has a sequence of a fragment of Vpr protein are useful in the same manner as pharmaceutical compositions comprising a fragment of Vpr protein or a non-Vpr protein that has a sequence of a fragment of Vpr protein: for treating an individual having a pathology or condition characterized by hyperproliferating cells. Pharmaceutical compositions of the present invention are particularly useful for treating cancer characterized by solid tumors.

Thus, a further aspect of the present invention relates to a method of treating an individual suffering from a disease associated with hyperproliferating cells which comprises the step of administering to said individual an amount of nucleic acid that comprises a nucleotide sequence that encodes a fragment of Vpr protein or a non-Vpr protein that has a sequence of a fragment of Vpr protein operably linked to regulatory elements necessary for expression.

Nucleotide sequences that encode a fragment of Vpr protein or a non-Vpr protein that has a sequence of a fragment of Vpr protein operably linked to regulatory elements necessary for expression in the individual's cell may be delivered as pharmaceutical compositions using gene therapy strategies which include, but are not limited to, either viral vectors such as adenovirus or retrovirus vectors or direct nucleic acid transfer. Methods of delivery nucleic acids encoding proteins of interest using viral vectors are widely reported. A recombinant viral vector such as a retrovirus vector or adenovirus vector is prepared using routine methods and starting materials. The recombinant viral vector comprises a nucleotide sequence that encodes a fragment of Vpr protein or a non-Vpr protein that has a sequence of a fragment of Vpr protein. Such a vector is combined with a pharmaceutically acceptable carrier or diluent. The resulting pharmaceutical preparation may be administered to an individual. Once an individual is infected with the viral vector, a fragment of Vpr protein or a non-Vpr protein that has a sequence of a fragment of Vpr protein is produced in the infected cells.

Alternatively, a molecule which comprises a nucleotide sequence that encodes fragment of Vpr protein or a non-Vpr protein that has a sequence of a fragment of Vpr protein can be administered as a pharmaceutical composition without the use of infectious vectors. The nucleic acid molecule may be DNA or RNA, preferably DNA. The DNA molecule may be linear or circular, it is preferably a plasmid. The nucleic acid molecule is combined with a pharmaceutically acceptable carrier or diluent. Compositions and methods for delivering proteins to cells by direct DNA administration have been reported using a variety of protocols. Examples of such methods are described in U.S. Pat. Nos. 5,593,972, 5,739, 118, 5,580,859, 5,589,466, 5,703,055, 5,622,712, 5,459,127, 5,676,954, 5,614,503, and PCT application PCT/US95/ 12502, which are each incorporated herein by reference. Compositions and methods for delivering proteins to cells by direct DNA administration are also described in PCT/ US90/01515, PCT/US93/02338, PCT/US93/048131, and PCT/US94/00899, which are each incorporated herein by reference. In addition to the delivery protocols described in those applications, alternative methods of delivering DNA are described in U.S. Pat. Nos. 4,945,050 and 5,036,006, which are both incorporated herein by reference. Examples of recombinant adenoviral vectors useful to deliver nucleic acid sequences are described in U.S. Pat. Nos. 5,756,283 and 5,707,618, which are each incorporated herein by reference. Nucleic acid molecules can also be delivered using liposome-mediated DNA transfer such as that which is described in U.S. Pat. Nos. 4,235,871, 4,241,046 and 4,394, 448, which are each incorporated herein by reference.

According to some methods of the invention, the nucleic acid molecules may be administered to an individual at a site on said individual's body by a route of administration selected from the group consisting of: intramuscularly, intranasally, intraperatoneally, subcutaneously, intradermally, or topically or by lavage to mucosal tissue selected from the group consisting of vaginal, rectal, urethral, buccal and sublingual. Some preferred routes of administration include intradermal, subcutaneous, intraperitoneal, intramuscular, and oral.

According to some methods of the invention, the DNA is plasmid DNA.

According to some embodiments of the invention, the promoters is selected form the group consisting of: Simian Virus 40 (SV40), Mouse Mammary Tumor Virus (MMTV) promoter, Human Immunodeficiency Virus (HIV) such as the HIV Long Terminal Repeat (LTR) promoter, Moloney virus, AI, V, Cytomegalovirus (CMV) such as the CMV immediate early promoter, Epstein Barr Virus (EBV). Rous Sarcoma Virus (RSV) as well as promoters from human genes such as human Actin, human Myosin, human Hemoglobin, human muscle creatine and human metalothionein.

According to some embodiments of the invention, the polyadenylation signal is selected from the group consisting of an SV40 polyadenylation signal and bovine growth hormone polyadenylation signal.

According to some methods of the invention, the DNA molecule is administered with a composition which facilitates uptake of DNA molecules by a cell. In some embodiments, the nucleic acid molecule is delivered to the cells in conjunction with the administration of a co-agent. Examples of co-agents are described in U.S. Pat. Nos. 5,593,972, 5,739,118 and International Application Serial Number PCT/US94/00899 filed Jan. 26, 1994, which are each incorporated herein by reference. The co-agents which are administered in conjunction with nucleic acid molecules may be administered as a mixture with the nucleic acid molecule or administered separately simultaneously, before, or after administration of nucleic acid molecules. In some embodiments, co-agents may be cationic lipids, including but not limited to, those described in U.S. Pat. No. 5,703, 055. Examples of other co-agents include growth factors, cytokines and lymphokines such as α-interferon, gamma-interferon, platelet derived growth factor (PDGF), TNF, epidermal growth factor (EGF). IL-1, IL-2, IL-4, IL-6, IL-8, IL-10 and IL-12 as well as fibroblast growth factor, surface active agents such as immune-stimulating complexes (ISCOMS). Freund's incomplete adjuvant, LPS analog including monophosphoryl Lipid A (MPL), Cholera toxin, cobra toxin, saponins, muramyl peptides, quinone analogs and vesicles such as squalene and squalene, and hyaluronic acid. In some embodiments, an immunomodulating protein may be used as a co-agent. Preferred compositions that facilitate uptake of DNA molecule by a cell are selected from the group consisting of: cationic lipids, liposomes and local anesthetics. In some preferred embodiments, the DNA molecule is administered with bupivacaine. In some embodiments, multiple co-agents are used. The co-agents which are administered in conjunction with nucleic acid molecules may be administered as a mixture with the nucleic acid molecule or administered separately simultaneously, before or after administration of nucleic acid molecules.

According to the invention, the pharmaceutical composition comprising a nucleic acid sequence that encodes a fragment of Vpr protein or a non-Vpr protein that has a sequence of a fragment of Vpr protein may be administered directly into the individual or delivered ex vivo into removed cells of the individual which are reimplanted after administration. By either route, the genetic material is introduced into cells which are present in the body of the individual. Preferred routes of administration include intramuscular, intraperitoneal, intradermal and subcutaneous injection. Alternatively, the pharmaceutical composition may be introduced by various means into cells that are removed from the individual. Such means include, for example, transfection, electroporation and microprojectile bombardment. After the nucleic acid molecule is taken up by the cells, they are reimplanted into the individual.

The pharmaceutical compositions according to the present invention comprise about 1 ng to about 10,000 μg of DNA. In some preferred embodiments, the pharmaceutical compositions contain about 2000 μg, 3000 μg, 4000 μg or 5000 μg of DNA. In some preferred embodiments, the pharmaceutical compositions contain about 1000 μg of DNA. In some preferred embodiments, the pharmaceutical compositions contain about 10 ng to about 800 μg of DNA. In some preferred embodiments, the pharmaceutical compositions contain about 0.1 to about 500 μg of DNA. In some preferred embodiments, the pharmaceutical compositions contain about 1 to about 350 μg of DNA. In some preferred embodiments, the pharmaceutical compositions contain about 25 to about 250 μg of DNA. In some preferred embodiments, the pharmaceutical compositions contain about 100 μg DNA.

The pharmaceutical compositions according to this aspect of the present invention are formulated according to the mode of administration to be used. One having ordinary skill in the art can readily formulate a nucleic acid molecule that encodes a fragment of Vpr protein or a non-Vpr protein that has a sequence of a fragment of Vpr protein. In cases where intramuscular injection is the chosen mode of administration, an isotonic formulation is used. Generally, additives for isotonicity can include sodium chloride, dextrose, mannitol, sorbitol and lactose. Isotonic solutions such as phosphate buffered saline may be used. Stabilizers include gelatin and albumin.

In a preferred embodiment, the DNA is administered by intramuscular injection. Bupivacaine, a well known and commercially available pharmaceutical compound, is administered prior to, simultaneously with or subsequent to the genetic construct. Bupivacaine and the genetic construct may be formulated in the same composition. Bupivacaine is particularly useful in view of its many properties and activities when administered to tissue. Bupivacaine is related chemically and pharmacologically to the aminoacyl local anesthetics. It is a homologue of mepivacaine and related to lidocaine. Bupivacaine renders muscle tissue voltage sensitive to sodium challenge and effects ion concentration within the cells. A complete description of bupivacaine's pharmacological activities can be found in Ritchie, J. M. and N. M. Greene. The Pharmacological Basis of Therapeutics, Eds.: Gilman, A. G. et al, 8th Edition. Chapter 15: 3111, which is incorporated herein by reference. Bupivacaine and compounds that display a functional similarity to bupivacaine are preferred in the method of the present invention.

Bupivacaine-HCl is chemically designated as 2-piperidinecarboxamide, 1-butyl-N-(2,6-dimethylphenyl) monohydrochloride, monohydrate and is widely available commercially for pharmaceutical uses from many sources including Astra Pharmaceutical Products Inc. (Westboro, Mass.) and Sanofi Winthrop Pharmaceuticals (New York, N.Y.). Bupivacaine is commercially formulated with and without methylparaben and with or without epinephrine. Any such formulation may be used. It is commercially available for pharmaceutical use in concentrations of 0.25%, 0.5% and 0.75% which may be used on the invention. Alternative concentrations which elicit desirable effects may be prepared if desired. According to the present invention, about 250 μg to about 10 mg of bupivacaine is administered. In some embodiments, about 250 μg to about 7.5 mg is administered. In some embodiments, about 0.50 mg to about 5.0 mg is administered. In some embodiments, about 1.0 mg to about 3.0 mg is administered. In some embodiments about 5.0 mg is administered. For example, in some embodiments about 50 μl to about 2 ml, preferably 50 μl to about 1500 μl and more preferably about 1 ml of 0.5% bupivacaine-HCl and 0.1% methylparaben in an isotonic pharmaceutical carrier is administered at the same site as the nucleic acid molecule before, simultaneously with, or after the nucleic acid molecule is administered. Similarly, in some embodiments, about 50 μl to about 2 ml, preferably 50 μl to about 1500 μl and more preferably about 1 ml of 0.5% bupivacaine-HCl in an isotonic pharmaceutical carrier is administered at the same site as the nucleic acid molecule before, simultaneously with, or after the nucleic acid molecule is administered. Bupivacaine and any other similarly acting compounds, particularly those of the related family of local anesthetics, may be administered at concentrations which provide the desired facilitation of uptake of genetic constructs by cells.

In some embodiments of the invention, the individual is first subjected to bupivacaine injection prior to administration of the nucleic acid molecule by intramuscular injection. That is, for example, up to about a week to ten days prior to administration of the nucleic acid molecule, the individual is first injected with bupivacaine. In some embodiments, prior to administration of the nucleic acid molecule, the individual is injected with bupivacaine about 1 to 5 days before administration of the genetic construct. In some embodiments, prior to administration of the nucleic acid molecule, the individual is injected with bupivacaine about 24 hrs before administration of the genetic construct. Alternatively, bupivacaine can be injected simultaneously, minutes before or after administration of the nucleic acid molecule.

Accordingly, bupivacaine and the genetic construct may be combined and injected simultaneously as a mixture. In some embodiments, the bupivacaine is administered after administration of the genetic construct. For example, up to about a week to ten days after administration of the genetic construct, the individual is injected with bupivacaine. In some embodiments, the individual is injected with bupivacaine about 24 hrs after administration of the nucleic acid molecule. In some embodiments, the individual is injected with bupivacaine about 1 to 5 days after administration of the nucleic acid molecule. In some embodiments, the individual is administered bupivacaine up to about a week to ten days after administration of the nucleic acid molecule.

The present invention may be performed using local anesthetics as facilitators. In addition to bupivacaine, mepivacaine, lidocaine, procaine, carbocaine and methyl bupivacaine, other similarly acting compounds may be used.

The present invention relates to a method of inhibiting a cell from proliferating by arresting it in the cell cycle. The method comprises the step of contacting the cell with an amount of a fragment of Vpr protein comprises amino acids 19–35 and/or 74–89 or a non-Vpr protein that has a sequence of a fragment of Vpr protein which comprises amino acids 19–35 and/or 74–89 of Vpr protein or a nucleic acid molecule that encodes a fragment of Vpr protein which comprises amino acids 19–35 and/or 74–89 or a non-Vpr protein that has a sequence of a fragment of Vpr protein which comprises amino acids 19–35 and/or 74–89 of Vpr protein sufficient to inhibit cell proliferation.

A fragment of Vpr protein or a non-Vpr protein that has a sequence of a fragment of Vpr protein may be delivered by a variety of means. In some embodiments of the invention, it is combined with cells as a protein. In some embodiments, the fragment of Vpr protein or non-Vpr protein that has a sequence of a fragment of Vpr protein may be added directly to cell culture medium. A fragment of Vpr protein or a non-Vpr protein that has a sequence of a fragment of Vpr protein may be produced from widely available starting materials using well known techniques, such as described above. A preferred concentration range of the fragment of Vpr protein or a non-Vpr protein that has a sequence of a fragment of Vpr protein used is about 1μg/ml to 1 mg/ml. Alternatively, a fragment of Vpr protein or a non-Vpr protein that has a sequence of a fragment of Vpr protein may be contacted with a cell by introducing into the cell a nucleic acid molecule which comprises a nucleic acid sequence encoding a fragment of Vpr protein or a non-Vpr protein that has a sequence of a fragment of Vpr protein. In such embodiments, the nucleic acid sequence may be introduced as part of an HIV particle, part of a recombinant infectious expression system particle or part of an expression vector such as a plasmid. Additionally linear DNA or RNA may also be introduced into the cell in an expressible form. In some embodiments, expression vectors or other nucleic molecules designed to produce a fragment of Vpr protein or a non-Vpr protein that has a sequence of a fragment of Vpr protein in cultured cells are used. Such an expression system may include a vector system to introduce the genetic material or the nucleic acid molecule may be introduced by other standard techniques such as transfection, electroporation or microprojectile bombardment.

Another aspect of the invention relates to methods of identifying compounds which inhibit Vpr protein from binding to the full length precursor protein encoded by the gag gene (p55) and to specific smaller proteins generated when p55 is processed by HIV protease. In particular, it has been discovered that Vpr protein binds to p55 precursor Gag protein at the domain which corresponds to the p6 protein which is produced after p55 is processed by the HIV protease. In particular, amino acids 17–36 of HIV-1 Vpr protein are involved in interactions with the p6 domain of Gag pro protein. Fragments of Vpr protein that comprise amino acids 17–36 are useful in assays to identify compounds which inhibit HIV-1 viral assembly. Similarly, non-Vpr proteins that comprise amino acids 17–36 of Vpr protein are useful in assays to identify compounds which inhibit HIV-1 viral assembly. Such compounds are useful as anti-HIV agents.

The methods comprise the steps of first contacting, in the presence of a test compound, a fragment of Vpr protein that comprise amino acids 17–36 or a non-Vpr protein that comprise amino acids 17–36 of Vpr protein, and a protein having a domain corresponding to the p6 domain of the HIV-1 Gag protein, then determining the level of binding and comparing the level of binding to the level of binding that occurs in the absence of the test compound. In preferred embodiments, the protein having a domain corresponding to the p6 domain of the HIV-1 Gag protein is either p6 or p55, the full length Gag preprocessed polyprotein. Compounds which interfere with the binding of Vpr protein amino acids 17–36 and the p6 domain of p55 are useful to impede production of HIV. Accordingly, such compounds are useful to inhibit production of fully virulent HIV particles; therefore such compounds will be useful as anti-HIV therapeutics alone or as part of a multi-faceted anti-HIV drug regimen which includes other therapeutics.

To practice these aspects of the invention, a fragment of Vpr protein that comprise amino acids 17–36 or a non-Vpr protein that comprise amino acids 17–36 of Vpr protein, and a protein having a domain corresponding to the p6 domain of the HIV-1 Gag protein are contacted in the presence of a test compound. The level of binding of the proteins is determined. The resultant level of binding is compared to the known level of binding that occurs when both proteins are contacted with each other in the absence of the test protein. In the absence of a compound that interferes with the binding, the two proteins will bind. As a control, the fragment of Vpr protein that comprise amino acids 17–36 or the non-Vpr protein that comprise amino acids 17–36 of Vpr protein, and the protein having the p6 domain of the HIV-1 Gag protein are contacted in the absence of a test compound.

Test compound is provided, preferably in solution. Serial dilutions of test compounds may be used in a series of assays. Test compound may be added at concentrations from $0.01\mu M$ to 1M. A preferred range of final concentrations of a test compound is from $10\mu M$ to $100\mu M$.

Production of a fragment of Vpr protein that comprise amino acids 17–36 or a non-Vpr protein that comprise amino acids 17–36 of Vpr protein is described above. A preferred concentration range of the fragment of Vpr protein or non-Vpr protein is about $1\mu g/ml$ to 1 mg/ml. A preferred concentration of fragment of Vpr protein or non-Vpr protein is about 50 $\mu g/ml$.

The full length precursor protein encoded by the gag gene, p55, may be produced by routine means using readily available starting materials following the teachings described above for production of Vpr protein. One having ordinary skill in the art can, using well known techniques, obtain a DNA molecule encoding the Gag protein and insert that DNA molecule into a commercially available expression vector for use in well known expression systems. One having ordinary skill in the art can, using well known techniques, isolate the p55 protein produced in such expression systems. Similarly, p6 can be produced and isolated. For example, p55 can be produced as described herein and processed by one having ordinary skill in the art using HTV protease to produce and isolate p6 without undue experimentation. Alternatively, one having ordinary skill in the art can, using well known techniques, obtain a DNA molecule encoding the p55 protein and insert a portion of the DNA molecule that encodes p6 into a commercially available expression vector for use in well known expression systems. One having ordinary skill in the art can, using well known techniques, isolate the protein produced in such expression systems.

A preferred concentration range of Gag protein used is about 1 $\mu g/ml$ to about 1 mg/ml.

The means to detect the presence of a protein product are routine and include enzyme assays and ELISA assays. One having ordinary skill in the art can detect the presence or absence of a protein using well known methods. One having ordinary skill in the art can readily appreciate the multitude of ways to practice a binding assay to detect compounds which modulate the binding of the fragment of Vpr protein or non-Vpr protein, and the protein comprising the Gag p6 domain. For example, antibodies are useful for immunoassays which detect or quantitate the fragment of Vpr protein or non-Vpr protein bound to the protein comprising the Gag p6 domain. The immunoassay typically comprises incubating the fragment of Vpr protein or non-Vpr protein, and the protein comprising the Gag p6 domain to allow protein-protein binding in the presence of a detectably labeled high affinity antibody capable of selectively binding to either the fragment of Vpr protein or non-Vpr protein, or the protein comprising the Gag p6 domain, and detecting the labeled antibody which is bound to the protein. Various immunoassay procedures are described in *Immunoassays for the 80's*. A. Voller et al., Eds., University Park, 1981.

In this aspect of the invention, the antibody or either the fragment of Vpr protein or non-Vpr protein, or the protein comprising the Ga p6 domain may be added to nitrocellulose, or other solid support which is capable of immobilizing proteins. The support may then be washed with suitable buffers followed by treatment with the detectably labeled antibody specific for the fragment of Vpr protein or non-Vpr protein, or the protein comprising the Gag p6 domain. The solid phase support may then be washed with the buffer a second time to remove unbound antibody. The amount of bound label on said solid support may then be detected by conventional means.

By "solid phase support" or "carrier" is intended any support capable of binding antigen or antibodies. Well-known supports or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support configuration may be spherical, as in a bead, or cylindrical, as in the inside surface of a test tube, or the external surface of a rod. Alternatively, the surface may be flat such as a sheet, test strip, etc. Those skilled in the art will know many other suitable carriers for binding antibody or antigen, or will be able to ascertain the same by use of routine experimentation.

The binding activity of a given lot of antibodies may be determined according to well known methods. Those skilled in the art will be able to determine operative and optimal assay conditions for each determination by employing routine experimentation.

Positive control assays may be performed in which no test compound is added.

One of the ways in which the antibodies can be detectably labeled is by linking the same to an enzyme and use in an enzyme immunoassay (EIA), or enzyme-linked immunosorbent assay (ELISA). This enzyme, when subsequently exposed to its substrate, will react with the substrate generating a chemical moiety which can be detected, for example, by spectrophotometric, fluorometric or by visual means. Enzymes which can be used to detectably label the antibody include, but are not limited to, malate dehydrogenase, staphylococcal nuclease, delta-5-steroid, isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the antibody, it is possible to detect it through the use of a radioimmunoassay (RIA) (see, for example. Work. T. S., et al., *Laboratory Techniques and Biochemistry in Molecular Biology*, North Holland Publishing Company, N.Y., 1978. The radioactive isotope can be detected by such means as the use of a gamma counter or a scintillation counter or by autoradiography. Isotopes which are particularly useful for the purpose of the present invention are: $^3$H, $^{125}$I, $^{131}$I, $^{35}$S, $^{14}$C, and, preferably, $^{125}$I.

It is also possible to label the antibody with a fluorescent compound. When the fluorescent labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence-emitting metals such as $^{152}$Eu, or others of the lanthanide series. These metals can be attached to the TNF-specific antibody using such metal chelating groups as diethylenetriaminepentaacetic acid (DTPA) or ethylenediamine-tetraacetic acid (EDTA).

The antibody also can be detectably labeled by coupling to a chemiluminescent compound. The presence of the chemiluminescently labeled antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. Detection of the Vpr-specific antibody or tile antibody that binds to the Gag-derived protein may be accomplished by a scintillation counter, for example, if the detectable label is a radioactive gamma emitter, or by a fluorometer, for example, if the label is a fluorescent material.

In the case of an enzyme label, the detection can be accomplished by colorometric methods which employ a substrate for the enzyme. Detection may also be accomplished by visual comparison of the extent of enzymatic reaction of a substrate in comparison with similarly prepared standards.

As can be readily appreciated, one of the viral proteins may also be detectable and serve as a reporter molecule instead of or in addition to the antibody.

The components of the assay may be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested and a quantity of detectably labeled soluble antibody is added to permit detection and/or quantitation of the ternary complex formed between solid-phase antibody, antigen, and labeled antibody.

Typical and preferred immunometric assays include "forward" assays in which the antibody bound to the solid phase is first contacted with the one of the viral proteins to immobilize it. The second viral protein is added in the presence of the test compound. After a suitable incubation period, the solid support is washed to remove unbound protein. A second antibody is then added which is specific for the second viral protein. The second antibody is preferably detectable. After a second incubation period to permit the labeled antibody to complex with the second viral protein bound to the solid support through the unlabeled antibody and first viral protein, the solid support is washed a second time to remove the unreacted labeled antibody. This type of forward sandwich assay may be a simple "yes/no" assay to determine whether binding has occurred or may be made quantitative by comparing the measure of labeled antibody with that obtained in a control. Such "two-site" or "sandwich" assays are described by Wide, *Radioimmune Assay Method*, Kirkham. Ed., E. & S. Livingstone; Edinburgh. 1970, pp. 199–206).

Other type of "sandwich" assays are the so-called "simultaneous" and "reverse" assays. A simultaneous assay involves a single incubation step wherein the antibody bound to the solid support and labeled antibody, both viral protein and the test compound are added at the same time. After the incubation is completed, the solid support is washed to remove uncomplexed proteins. The presence of labeled antibody associated with the solid support is then determined as it would be in a conventional "forward" sandwich assay.

In the "reverse" assay, stepwise addition first of a solution of labeled antibody to the viral proteins followed by the addition of unlabeled antibody bound to a solid support after a suitable incubation period, is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays. In one embodiment, a combination of antibodies of the present invention specific for separate epitopes may be used to construct a sensitive three-site immunoradiometric assay.

In some preferred embodiments, an anti-Vpr antibody is fixed to a solid phase. Vpr protein is contacted with the fixed antibody to form a complex. The complex is contacted with the Gag p6 protein in the presence of a test compound. Antibodies that bind to the Gag p6-containing protein are then added. The solid phase is washed to removed unbound material. A control assay is performed in an identical manner except that no test compound is used. Detection of the antibodies that bind to the Gag p6 protein indicates that Vpr and Gag proteins are capable of binding to each other in the presence of the test compound. Accordingly, failure to detect that antibodies that bind to the Vpr-derived protein indicates that the test compound inhibits binding of Vpr and Gag proteins. Quantifying the level of binding in the presence and absence of test compound allows for the measurement of the extent of modulation that the test compound can cause on Vpr binding to a Gag-derived protein.

In some preferred embodiments, antibodies that bind to the Gag-derived protein are fixed to a solid phase. Gag-derived protein is contacted with the fixed antibody to form a complex. The complex is contacted with the Vpr-derived protein in the presence of a test compound. Antibodies specific for the vpr-derived protein are then added. The solid phase is washed to removed unbound material. A control assay is performed in an identical manner except that no test compound is used. Detection of the antibodies that bind to Vpr-derived protein indicates that the Vpr-derived and Gag-derived proteins are capable of binding to each other in the presence of the test compound. Accordingly, failure to detect that antibodies that bind to Vpr-derived protein indicates that the test compound inhibits binding of Vpr and Gag-derived proteins. Quantifying the level of binding in the presence and absence of test compound allows for the measurement of the extent of modulation that the test compound can cause on Vpr binding to a Gag-derived protein.

A further aspect of the present invention relates to kits for practicing the above described method of identifying compounds which inhibit Vpr protein binding to the p6 domain of Gag protein. Kits according to this aspect of the invention comprises the a first container comprising a fragment of Vpr protein that comprise amino acids 17–36 or a non-Vpr protein that comprise amino acids 17–36 of Vpr protein, a second container comprising a Gag-derived protein which comprises the p6 domain. Additionally, to practice the above defined method, means are required to distinguish a fragment of Vpr protein or a non-Vpr protein bound to the Gag-derived protein from unbound fragments of Vpr protein or non-Vpr proteins and the Gag-derived protein. In a preferred embodiment of this aspect of the invention, a third container comprising an antibody that specifically binds to either the fragment of Vpr protein or a non-Vpr protein or to the Gag-derived protein is provided. At least one of the contained components, preferably the antibody, may be conjugated with an agent, such as those described above, which allows its presence to be detected. In another preferred embodiment of this aspect of the invention, a fourth container is provided which contains an antibody that specifically binds to either the fragment of Vpr protein or non-Vpr protein, or the Gag-derived protein, but not the protein which is bound by the antibody in the third container. At least one of the contained components, preferably the antibody, may be conjugated with an agent, such as those described above, which allows its presence to be detected.

Some aspects of the invention relate to pharmaceutical compositions, drug delivery systems and methods for specifically delivering fusion proteins that include Vpr protein amino acid sequences 17–36 linked to a biologically active protein. Viral particles comprising cell specific envelope proteins and p24 bound to fusion proteins that include Vpr protein amino acid sequences 17–36 linked to a biologically active protein may be produced. Such particles will deliver the fusion proteins that include Vpr protein amino acid sequences 17–36 linked to a biologically active protein to the cells for which the envelope is specific. The fusion proteins that include Vpr protein amino acid sequences 17–36 linked to a biologically active protein, and thus the biologically active protein, is thus delivered to cells. The present invention relates to compositions useful for delivering fusion proteins that include Vpr protein amino acid sequences 17–36 linked to a biologically active protein into specifically targeted cells. The composition comprise fusion proteins that include Vpr protein amino acid sequences 17–36 linked to a biologically active protein, p24 and a cell-type specific coat protein assembled as a particle which is a drug delivery particle that can specifically deliver fusion proteins that include Vpr protein amino acid sequences 17–36 linked to a biologically active protein cells that the coat protein binds to. The present invention relates to the particles, to the pharmaceutical compositions that comprise the particles and pharmaceutically acceptable carriers, to the nucleic acid molecules that encode the components, to the expression vectors and host cells that contain the nucleic acid molecules and to the methods of producing and using the compositions.

To prepare a drug delivery particle of the invention, the envelope protein (Env) of a retrovirus is chosen based upon the cell type such a retrovirus infects. Cell specific envelope proteins are well known. Cells are co-transfected with a nucleic acid molecule that encodes the desired Env, a nucleic acid molecule that encodes fusion proteins that include Vpr protein amino acid sequences 17–36 linked to a biologically active protein, a nucleic acid molecule that encodes p24 or a nucleic acid molecule that encodes the full length Gag precursor plus the HIV protease. Expression of these sequences will result in the proteins thus encoded being produced and assembly of the drug delivery particle. Noncoding RNA may also be provided for safety since the assembling particle will package RNA.

Biologically active proteins which can be used in fusion proteins include cytokines, lymphokines, structural proteins such as dystrophins, other therapeutic proteins and proteins which are useful as immune targets.

Another aspect of the invention arises from the identification of amino acids 17–36 and 59–84 of HIV-1 Vpr protein as being involved in nuclear localization of Vpr protein in HIV-1 infected cells. According to the invention, fragments of Vpr protein that comprise amino acids 17–36 and/or 59–84 can be conjugated to compounds in order to deliver such compounds to the nucleus of a cell. In some embodiments, the compounds is a protein or peptide and the conjugated compound is a fusion protein. Similarly, non-Vpr proteins that comprise amino acids 17–36 and or 59–84 of Vpr protein can be conjugated to compounds in order to deliver such compounds to the nucleus of a cell.

The nuclear localization of compounds is desirable, for example, when such compounds are associated with DNA expression. Accordingly, the effectiveness of compounds which modulate DNA expression including DNA binding compounds, polymerases and polymerase inhibitors, transcription factors, operators, repressors activators and the like can be increased by delivering them in combination with Vpr, fragments of Vpr protein that comprise amino acids 17–36 and/or 59–84 or non-Vpr proteins that comprise fragments of Vpr protein that comprise amino acids 17–36 and/or 59–84. The effectiveness is increased due to an increase in the delivery of such compounds to the nucleus of the cell, the site where the compounds are active. Similarly, the compounds may be antisense compounds such as antisense oligonucleotides which, when delivered to the nucleus, can inhibit transcription of genes being expressed in the nucleus. According to another embodiment of the invention, the compound is a DNA molecule, such as a plasmid, which includes coding sequences operably linked to regulatory elements needed for gene expression. By conjugating it to Vpr, fragments of Vpr protein that comprise amino acids 17–36 and/or 59–84 or non-Vpr proteins that comprise fragments of Vpr protein that comprise amino acids 17–36 and/or 59–84, the DNA molecule is delivered to the nucleus where coding sequences can be expressed. In DNA transfer protocols, such as those incorporated herein by reference above, DNA-based vaccines and gene therapeutics are delivered as active agents. In such protocols, a fraction of the total DNA administered and taken up by the cell is delivered to the nucleus and expressed. Conjugation of such active agent DNA molecules to Vpr, fragments of Vpr protein that comprise amino acids 17–36 and/or 59–84 or non-Vpr proteins that comprise fragments of Vpr protein that comprise amino acids 17–36 and/or 59–84 results in a greater proportion of DNA molecules translocated to the nucleus.

Conjugation of compounds to Vpr, fragments of Vpr protein that comprise amino acids 17–36 and/or 59–84 or non-Vpr proteins that comprise fragments of Vpr protein that comprise amino acids 17–36 and/or 59–84 can be accomplished by those of ordinary skill in the art routinely. For example, Vpr, fragments of Vpr protein that comprise amino acids 17–36 and/or 59–84 or non-Vpr proteins that comprise fragments of Vpr protein that comprise amino acids 17–36 and/or 59–84 may further comprise polycationic amino acid sequences such as polylysine heads or tails. The polycationic amino acid sequences can be covalently linked to the Vpr, fragments of Vpr protein that comprise amino acids 17–36 and/or 59–84 or non-Vpr proteins that comprise fragments of Vpr protein that comprise amino acids 17–36 and/or 59–84 and linked to the DNA molecules through ionic bonds between the polycation groups and the anionic backbone of the DNA. Accordingly, the present invention provides improved DNA administration technology by providing DNA molecules associated with Vpr, fragments of Vpr protein that comprise amino acids 17–36 and/or 59–84 or non-Vpr proteins that comprise fragments of Vpr protein that comprise amino acids 17–36 and/or 59–84.

While the portions of the disclosure herein which relate to therapeutic compositions and methods primarily relates to therapeutics and methods of treating humans. the compositions and methods of the present invention can be applied to veterinary medical uses as well. It is within the scope of the present invention to provide methods of treating non-human as well as human individuals. Accordingly, the present invention relates to a method of treating all animals, particularly mammalian species including human, bovine, ovine, porcine, equine, canine and feline species.

EXAMPLE

Summary

The vpr gene product of human immunodeficiency virus type 1 (HIV-1) is a virion associated protein that is essential for efficient viral replication in monocyte/macrophages, Vpr is primarily localized in the nucleus when expressed in the absence of other viral proteins, Vpr is packaged efficiently into viral particles through interactions with the p6 domain of the Gag precursor polyprotein p55gag. We developed a panel of expression vectors encoding Vpr molecules mutated in the amino terminal helical domain, leucine-isoleucine (LR) domain, and carboxy terminal domain to map the different functional domains and to define the interrelationships between virion incorporation, nuclear localization, cell cycle arrest, and differentiation functions of Vpr. We observed that substitution mutations in the N-terminal domain of Vpr impaired both nuclear localization and virion packaging, suggesting that the helical structure may play a vital role in modulating both of these biological properties. The LR domain was found to be involved in the nuclear localization of Vpr. In contrast, cell cycle arrest appears to be largely controlled by the C-terminal domain of Vpr. The LR and C-terminal domains do not appear to be essential for virion incorporation of Vpr. Interestingly, we found that two Vpr mutants harboring single amino acid substitutions (A30L and G75A) retained the ability to translocate to the nucleus but were impaired in the cell cycle arrest function. In contrast, mutation of Leu68 to Ser (L68S) resulted in a protein that localizes in the cytoplasm while retaining the ability to arrest host cell proliferation. We speculate that the nuclear localization and cell cycle arrest functions of Vpr are not interrelated and that these functions of Vpr are not interrelated and that these functions are mediated by separable putative functional domains of Vpr.

Introduction

To define the interrelationship between the different functions of Vpr we created a panel of expression vectors encoding vectors encoding mutant Vpr molecules. We tested a panel of Vpr mutants for their ability to arrest the cell cycle, to localize to the nucleus, to affect cellular differentiation, and to be packaged into virus-like particles. Our studies indicate that mutations in the amino-terminal acidic domain of Vpr with a predicted alpha-helical domain reduces virion packaging of Vpr, and alters its nuclear localization. We postulate that these impairments are likely due to reduced protein stability and/or structural conformation of the mutant Vpr proteins. Moreover, we also identified amino acid residues located in the LR motif which appear to control the nuclear localization. Finally, the C-terminal domain appears to control the cell cycle arrest activity of Vpr. Importantly, these studies demonstrate that nuclear localization and cell cycle arrest appear to be separable functions of Vpr.

Materials and Methods
Cells, Virus, and Expression Plasmids

The recombinant vaccinia virus vTF7-3, which synthesizes T7 RNA polymerase in infected cells was used for expression studies (Fuerst. T. R. et al., *Mol. Cell. Biol.,* 1987, 7: 2538–2544.). The genes encoding HIV-1 Gag polyprotein and Vpr were cloned downstream of the T7 promoter in pCDNA3 (Invitrogen) to generate pCDGag and pCDVpr expression plasmids, respectively (Macreadie, I. G. et al., *Proc. Natl. Acad. Sci. USA,* 1995, 92: 2770–2774.). HeLa and human embryonal rhabdomyosarcoma (RD) cells were used for transfection experiments and were maintained as monolayer cultures in Dulbecco's modified Eagle medium (DMEM) with 10% fetal bovine serum (FBS).

PCR-Mediated Mutagenesis

Overlap extension Polymerase Chain Reaction (PCR) (Ho et al., Gene, 1989, 77: 51–59) was used to introduce the site-specific mutations into HIV-1 vpr gene. Briefly, two PCR reactions were performed using HIV-1 proviral DNA as a template. The first round amplification products overlap at the mutation site. A second round of amplification was then carried out using the outer primer pair and a mixture of the first two reaction products as a template to generate a product containing the desired amino acid substitution mutation. The PCR products were digested with HindIII and XhoI (sites for which recognition sequences were incorporated into the outer primer pairs), cloned into pCDNA3, and sequenced to verify mutations and ensure the integrity of the vpr gene.

Infection and Transfection

HeLa cells ($1 \times 10^6$) grown in 35 mm dishes were infected with vTF7-3 at an m.o.i. of 10 for one hour in 5% $CO_2$ at 37° C. with rocking every 15 min. At the end of the incubation period, the virus inoculum was removed and the cells were washed once with PBS before transfection. Three to six $\mu g$ of plasmid DNA and 10 $\mu l$ of Lipofectin (BRL) were added to separate polystyrene tubes containing 0.1 ml of serum-free Opti-MEM and then combined. The mixture was incubated at room temperature for 15 min., supplemented with 0.6 ml of fresh opti-MEM, and layered onto infected cells for 3 hr. At 3 hours post-transfection, 0.8 ml of DMEM containing 10% heat inactivated FBS was added to the cultures and the incubation was continued for an additional 12 hours.

Transfection of RD cells wild type and mutant expression plasmids and examination of cell cycle distribution was performed as described previously (Mahalingham, S. et al., DNA Cell Biol., 1997, 16: 137–143). Briefly, RD cells were co-transfected with wild type and different mutant Vpr expression plasmids and pBabepuro (a vector that expresses puromycin resistance). Two days later, puromycin was added at a concentration of 2 $\mu g/ml$ to eliminate the untransfected cells and, seven to ten days post transfection, the RD cell nuclei were stained with propidium iodide for analysis of DNA content by flow cytometry.

Metabolic Labeling and Immunoprecipitation

Transfected HeLa cells were washed twice with PBS, starved for one hour in-DMEM lacking serum, methionine and cysteine, and then labeled with 200 $\mu Ci/ml$ (1.200 Ci/mmole) of $35_S$, protein labeling mix (NEN/Dupont). Labeled cells were lysed in 0.5 ml of RIPA buffer (50 mM TrisHCl pH7.6: 150 mM NaCl: 0.2% Triton X-100: 0.2% Deoxycholic acid: 0.1% SDS and 1 mM PMSF) on ice and then clarified by centrifugation at 15000 r.p.m. for 10 min. The clarified lysates were incubated with anti Vpr-antibody or HIV-1 antibody for 90 min. on ice. Protein A sepharose was added to antigen-antibody complexes and mixed by shaking at 4° C. for 90 min. The protein pellet was resuspended in 50 $\mu l$ of 1xsample buffer and heated at 100° C. for 3–5 min. after extensive washing in buffers containing high salt and BSA. A fraction of the protein sample was analyzed by SDS 12% PAGE. For fluorography, gels were soaked in 1M sodium salicylate containing 10% glycerol for 15 min., dried, and autoradiographed using Kodak, X-omat-AR film.

Analysis of Vpr Incorporation into Virus-like Particles Directed by HIV-1 gag

Recombinant vaccinia virus infected HeLa cells were transfected with HIV-1 Gag expression vector (pCDGag) together with wild type or mutant Vpr expression plasmids as described above. After overnight incubation, cells were labeled with 200 $\mu Ci/ml$ of $35_S$-protein labeling mix. The culture medium was collected and clarified by centrifugation at 15000 r.p.m. for 15 min. after five hours of continuous labeling. The clarified media was loaded into Centricon-30 concentrators (Amicon) which have a 30,000 mw size exclusion barrier and centrifuged at 3000 r.p.m. for 25 min. The virus-like particles attached to the filter were resuspended with 0.5 ml RIPA buffer. Immunoprecipitation was performed using anti Vpr-antiserum alone, HIV-1 antibody alone, or both antibodies to determine the presence of Vpr in the virus-like particles.

Immunofluorescence Assay

HeLa cells were maintained in DMEM containing 10% FBS and seeded onto poly-L-lysine coated coverslips at a density of $1 \times 10^6$ cells per dish (35 mm). Cells were infected with vTF7-3 and transfected as described above after 24 hrs. Sixteen to 24 hours after transfection, the cells were washed with PBS and fixed with methanol at room temperature for 30 min. The cells were then washed with PBS and incubated for 90 min. with primary antiserum (1:50). After washing with PBS the coverslips were incubated for 90 min. with FITC-conjugated affinity purified F(ab)'2 fragment of goat anti-rabbit IgG (ICN Biochemicals: Calif.) and washed six times with PBS. Coverslips were then counterstained for 5 min. with Evans Blue (0.02% in PBS: Sigma: St. Louis) then rewashed prior to mounting on glass slides using a fade-resistant mounting medium (Citiflour; England). All incubations were carried out at 37° C. in a humidification chamber.

Results

Construction of Vpr Mutants

In order to identify the domain(s) of Vpr involved in virion incorporation, nuclear localization, differentiation, and cell cycle arrest functions, we constructed a series of mutated versions of Vpr molecules. In designing these mutants, we targeted three putative structural regions in the Vpr sequence: i) N-terminal acidic domain containing a putative α-helix (amino acids 17–34): ii) leucine-isoleucine rich region (LR domain); and iii) carboxy terminal domain. Substitution mutations designed to affect specific amino acid residues were found to be highly conserved among Vpr sequences from different HIV-1 isolates (FIG. 1A). The amino-terminal domain contains five negatively charted residues (amino acid positions 17, 21, 24, 25, and 29) which are highly conserved. Structural analysis of the amino acid sequences in this region strongly predicts an amphipathic α-helix. Similar structures have been shown to be involved in protein-protein interactions and virion incorporation of viral proteins in other viruses. We utilized site specific mutations of these residues which would disrupt the predicted structure. Two of these residues (Glutamic acid 21 and 24) were substituted with proline, which has low potential for supporting an α-helical structure (FIG. 1B).

To explore the importance of the highly conserved alanine (Ala30) we replaced this nonpolar alanine with a bulky polar residue leucine and a hydroxyl amino acid serine to generate mutants A30L and A30S, respectively. In addition, another helical Vpr mutant was generated by replacing the four hydrophobic polar leucines (amino acid position 20, 22, 23 and 26) with small nonpolar alanines (α L-A). To investigate the role of a second helix, we generated a Vpr mutant A59P by chancing alanine at amino acid position 59 to proline. Three Vpr mutants carrying substitutions of leucine to styrene at amino acid positions 64, 67, and 68 (L64S, L67S, and L68S) were constructed to introduce mutations in the LR domain (FIG. 1B)

Histidine71, glycine75, and cysteine76 in the C-terminus of Vpr are highly conserved among different HIV-1 isolates, and in both Vpr and Vpx of HIV-2/SIV. Cysteine has been shown to play a major role in protein stabilization and in protein-protein interactions (Chae. H. Z. et al., *Proc. Natl. Acad. Sci. USA,* 1994, 91:702–7026; Creighton. T. E., Disulfide bonds and protein stability, *BioEssays,* 1988, 8: 57–63: and Doig, A. J. and D. H. Williams, *J. Mol. Biol.,* 1991, 217: 389–398.). We targeted His, Gly, and Cys residues for mutagenesis to evaluate the role of this motif on the expression, virion packaging, subcellular localization, and cell cycle arrest functions of HIV-1 Vpr (FIG. 1B). All the substitution Vpr mutants were generated by the overlap PCR method and subcloned into pCDNA3 mammalian expression vector as described in materials and methods. The resulting constructs were verified by DNA sequence analysis.

Effects of Mutations on the Expression and Virion Packaging of Vpr

We employed a vaccinia virus T7-RNA polymerase expression system (vTF7-3) to study the effect of mutations on expression of Vpr in cells and incorporation into virus-like particles directed by the HIV-1 gag gene. vTF7-3 infected HeLa cells were transfected with wild-type or mutant Vpr expression plasmids by the lipofectin method. Cells were labeled or two hours with 35S-methionine, lysed, immunoprecipitated with anti-Vpr antiserum, and analyzed by SDS-12% PAGE. As expected, the cells transfected with Vpr expression plasmids produced a 14 kDa protein (FIG. 1C). Transfection with each of the mutants resulted in detectable levels of Vpr in the cell lysate. Interestingly, slower migration of Vpr was noticed in cells transfected with the Vpr α L-A expression plasmid. Vpr mutants E21,24P and H71Y also resulted in slightly slower migration than wild-type (FIG. 1C). This difference in electrophoretic migration may have resulted from the altered conformation of mutant Vpr proteins relative to the wild-type polypeptide or changes in the hydrophobic face (α L-A) of the first helical domain (FIG. 1D).

To define the amino acid residues of Vpr that are required for virion incorporation, we tested several Vpr mutant molecules for the ability to be packaged into virus particles. We utilized a transient packaging system which is generated by the HIV-1 gag gene as we described previously (Mahalingham. S. et al., *Virology,* 1995, 207: 297–302; and Mahalingham, S. et al., *Proc. Natl. Acad. Sci. USA* 1995, 92: 3794–3798). In this assay, mutant Vpr expression plasmids are cotransfected with HIV-1 Gag expression vectors into vTF7-3 infected HeLa cells. After overnight transfection, the cells were labeled with 35S methionine and the virus-like particles that had been secreted into the culture medium were collected and concentrated using a Centricon30 concentrator. The amount of Vpr present in the virion and cell associated Vpr was then detected by immunoprecipitation.

Figure 2:
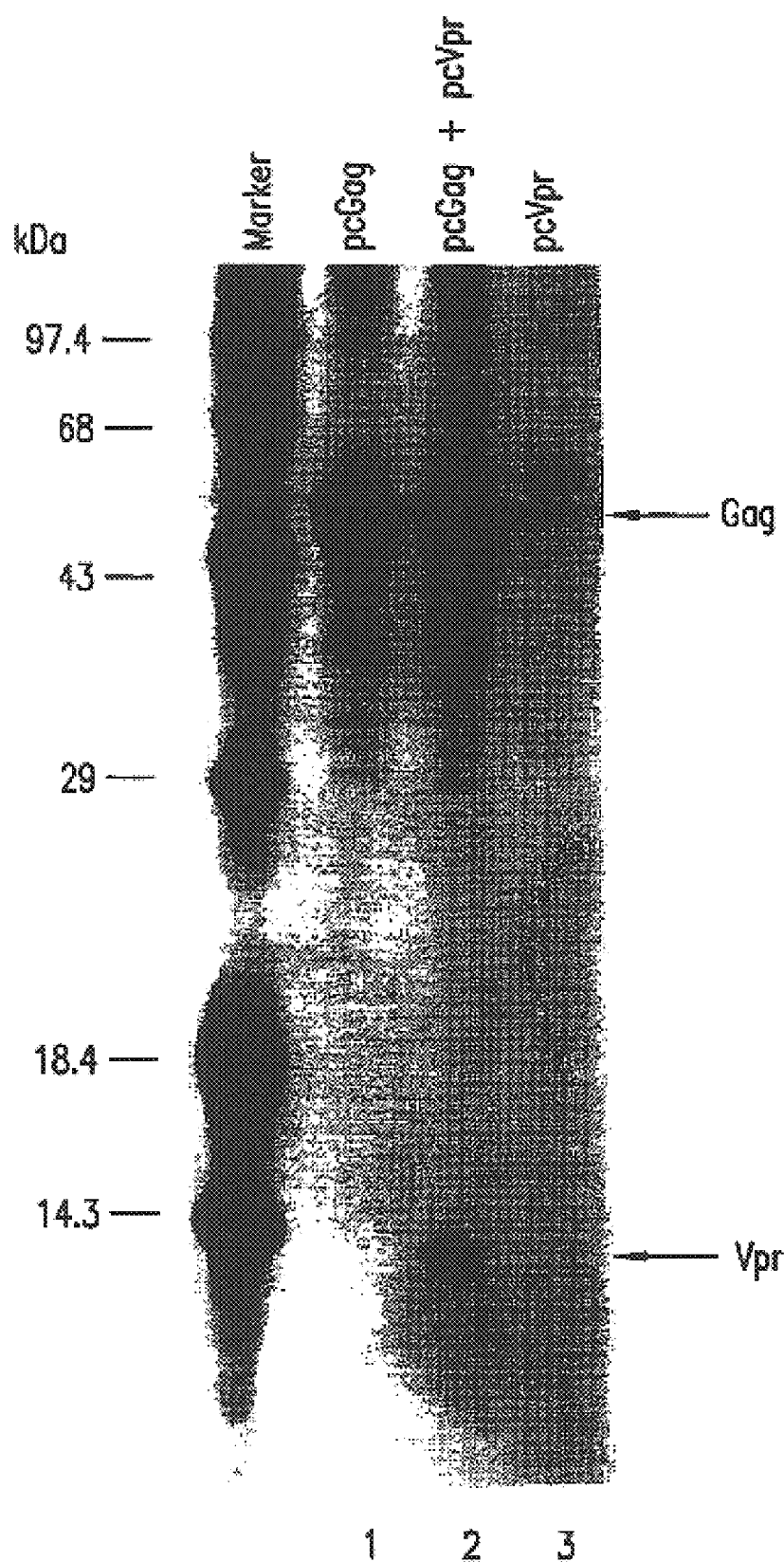
FIG. 2 shows incorporation of Vpr into virus-like particles directed by HIV-1 Gag. Cotransfection of pCDGag with wild type or mutant Vpr expression plasmids were carried out using vTF7-3-infected HeLa cells as described in Materials and Methods. Transfected cells were labeled with S35 protein labeling mix for 5 hours, the culture media was cleared by centrifugation, concentrated using Centricon 30 concentrators and virus-like particles were resuspended with RIPA buffer. Immunoprecipitation was carried out using anti-HIV and ant'-Vpr antiserum and analyzed by SDS-12% PAGE. The electrophoretic positions of Gag and Vpr are shown at the right and molecular mass markers are shown at the left in kilodaltons.

Expression of Gag resulted in a 55 kDa protein product in the cell culture supernatant and cotransfection of Gag and wild-type Vpr expression vectors resulted in the efficient packaging of Vpr into the virus like particles as expected (FIG. 2). In contrast, no Vpr could be detected in the virus-like particles from the cells cotransfected with Gag and Vpr mutants E21, 24P, αL-A, and A59P, despite detectable levels of expression in the cells (FIG. 1C and Table I). Vpr molecules with mutations at alanine 30 (A30S and A30L) and His71showed reduced levels of Vpr incorporation into virus-like particles. These results indicate that mutations at amino acid positions 64, 67, and 68 (L64S, L67S and L68S), Gly 75 and Cys 76 allow efficient packaging of Vpr into virus-like particles. Taken together with other studies these results support the importance of a putative helical domain with these additional mutants in the packaging of Vpr into HIV-1 virus particles.

Figures 1, 4A:
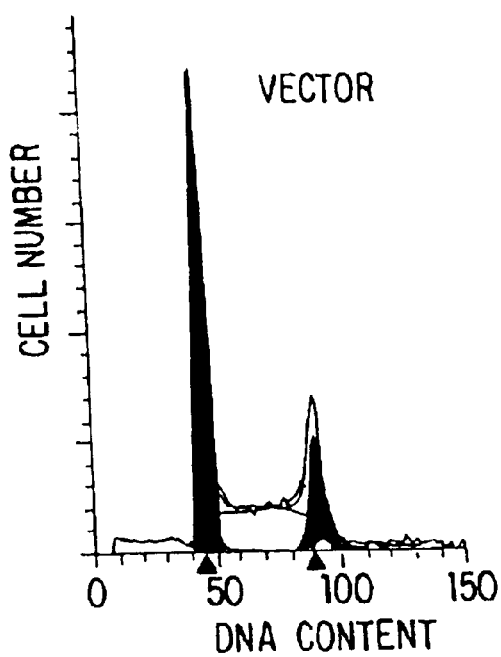
Figures 2, 4A:
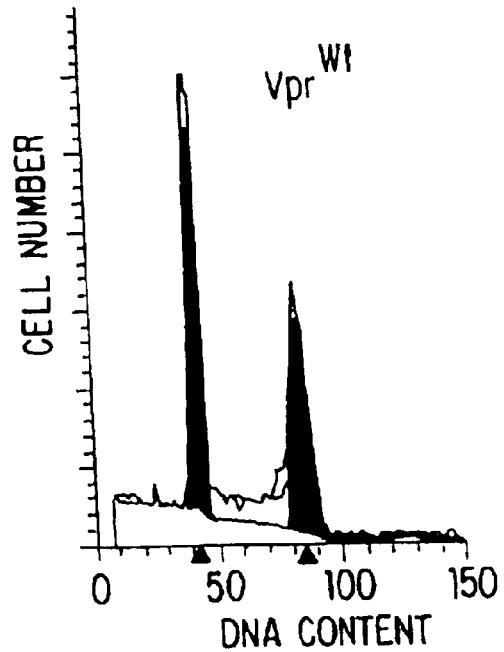
Figures 3, 4A:
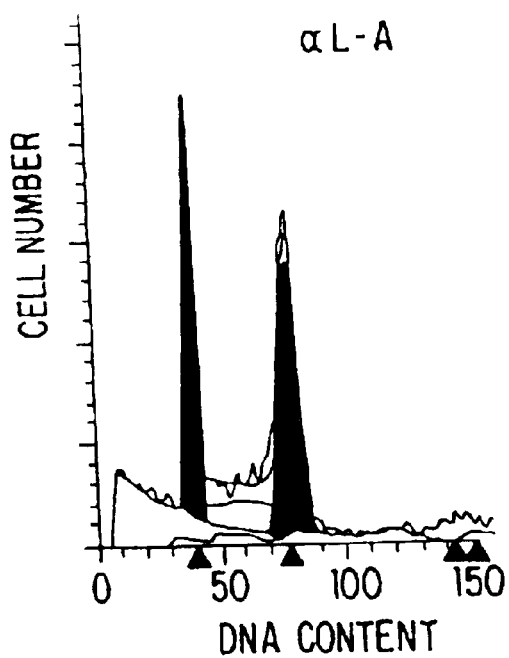

Substitution Mutational Analysis Reveals that Putative Helical and LR Domains are Necessary for Nuclear Transport of Vpr Previously it has been shown that Vpr localizes in the nucleus of infected and transfected cells in the absence of other viral proteins despite the lack of a canonical nuclear localization signal (DiMarzio, P. et al., *J. Virol.,* 1995, 69: 7909–7916; Lu, Y. et al., *J. Virol.,* 1993, 67: 6542–6550.; Mahalingham, S. et al., *Virology,* 1995, 210: 495–500; and Yao, X et al., *J. Virol.,* 1995, 69: 7032–7044). We analyzed our series of Vpr expression plasmids in order to define the amino acid residues required for nuclear localization as shown schematically in FIG. 1B. We transfected the mutant plasmids into vTF7-3 infected HeLa cells to determine the subcellular localization of the Vpr mutant molecules. After overnight transfection, the cells were fixed with methanol, labeled with antiVpr antiserum, and analyzed by an indirect immunofluorescence assay to evaluate the ability of various Vpr mutants to be targeted to the nucleus. As expected, the wild-type Vpr primarily localized in the nucleus of the transfected cells and no signal was observed in the vector transfected cells or in, wild-type Vpr transfected cells stained with preimmune serum (FIGS. 3A—3O). In contrast. Vpr mutants E21, 24P, α L-A, A59P, L67S, and L68S severely impaired the nuclear localization of Vpr as shown in FIGS. 3A—3O. The majority of cells expressing this mutant Vpr protein showed localization in the cytoplasm. Interestingly A30L and G75A mutant Vpr molecules retained the ability to localize in the nucleus (FIGS. 3A—3O). Mutants A30S, L64S, H71C, H71Y, and C76S had a notable amounts of protein in both the nucleus and cytoplasm (FIGS. 3A—3O). Mutants from the putative helical and LR domains exhibited notably different immunofluoresence patterns from that of wild-type Vpr. These results suggest that both N-terminal α-helix and LR domains are essential for the transport of Vpr into the nucleus.

Figures 4, 4A:
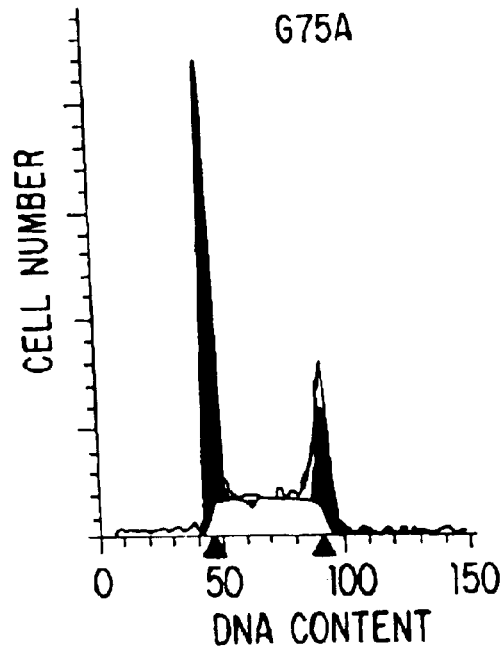
Figures 1, 4B:
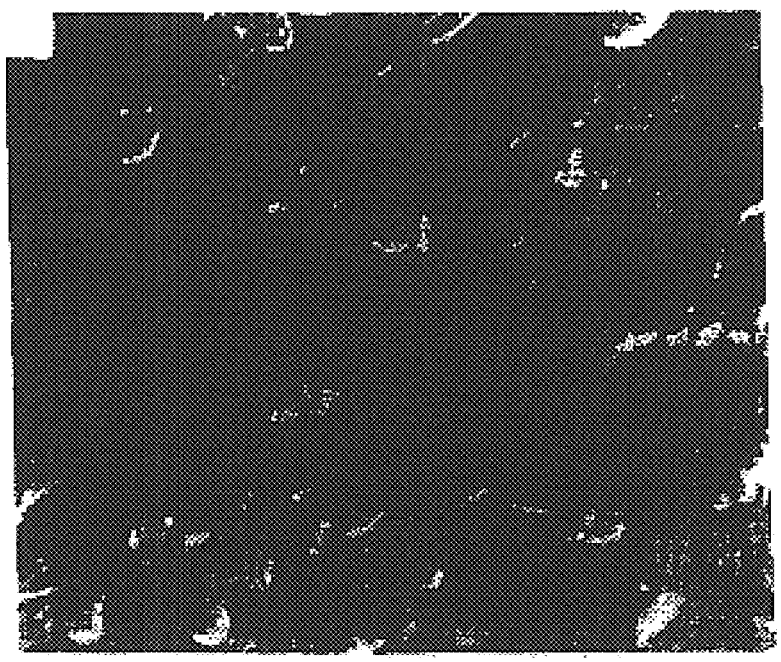
Figures 2, 4B:
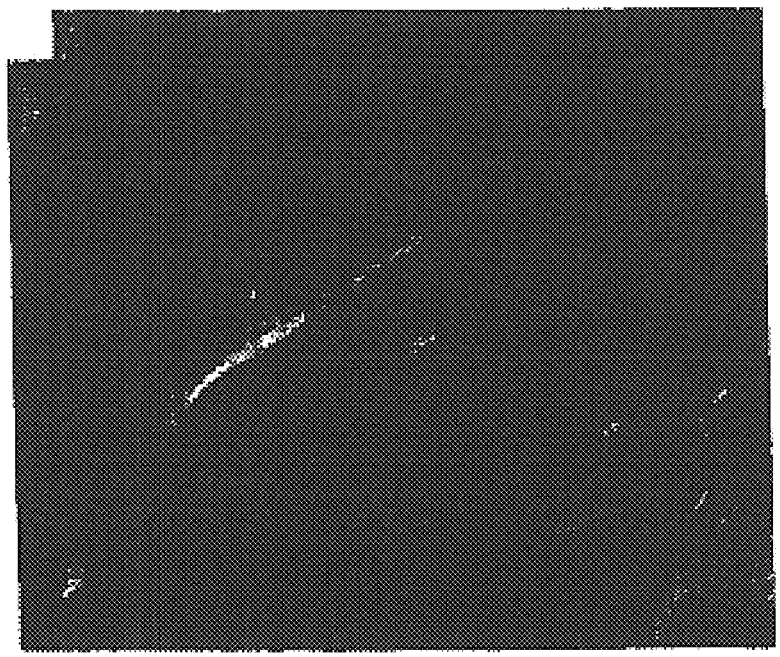

Amino Acid Residues of Vpr are Required for Cell Cycle Arrest at G2/M Phase of the Cell Cycle Previous studies have shown that Vpr induces cell differentiation (Levy D. N. et al., *Cell,* 1993, 72: 541–550.), growth arrest, and blocks the cell cycle at the G2/M phase (Rogel M. et al.,*J. Virol.,* 1995, 69: 882–888.). We analyzed a number of Vpr expression plasmids in order to identify the amino acid residues essential for cell cycle arrest and to define the interrelationship between the virion incorporation, subcellular localization, and the cell cycle arrest functions of Vpr. Human rhabdomyosarcoma cells were transiently transfected with Vpr expression plasmids and selected with puromycin. In parallel, cells were transfected with vector alone as controls. Transfected cells were fixed and stained with propidium iodide as whole cells to determine DNA content by flow cytometry. There was a dramatic increased in the proportion of cells in G2/M phase of cell division in cells transfected with wild-type Vpr expression plasmid (FIGS. 4A-1–4A-4), whereas vector transfected cells showed DNA content similar to that of unsynchronized cycling cells which were grown without puromycin (FIGS. 4A-1–4A-4). Cells expressing Vpr showed morphological changes such as increased adherence and growth arrest consistent with a terminal differentiated phenotype (FIGS. 4B-1–4B-2). These results confirm our previous report that Vpr expression in cells is capable of altering cell cycle distribution and morphological status.

Figure 4C:
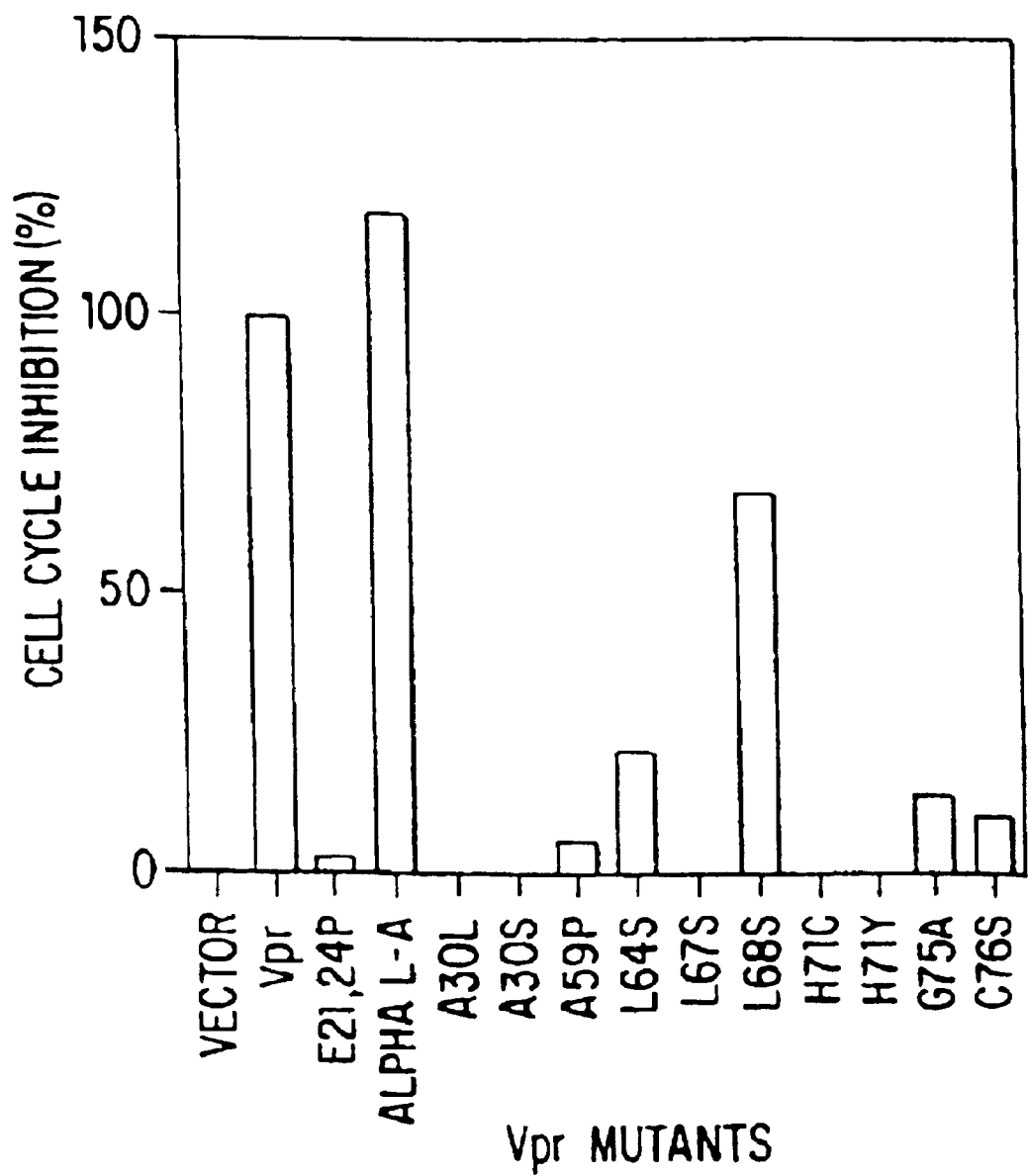

We measured the relative cell cycle blocking activity of each mutant Vpr molecule in the transient transfection assay to identify, the amino acid(s) important for cell cycle arrest. We noticed some experimental variability in the G2/M ratio of transfected cells with both wild-type and mutant Vpr upon repeated experimentation. Results of the analysis showed that Vpr mutants αL-A and L68S maintained cell cycle blocking activity (FIG. 4C). The cell cycle arrest activity of Vpr mutants E21, 24P, A30S, A30L, A59P, L64S, L67S, H71C, H71Y, G75A, and C76S was dramatically reduced (FIG. 4C). We believe that this finding is not likely to be due to instability of the protein, since these mutant molecules are stably expressed, Vpr mutants A30L and G75A were inactive in cell cycle arrest while retaining the wild-type nuclear localization. Of all the Vpr mutants, αL-A and L68S maintained cell cycle blocking activity, even though these mutant molecules localized in the cytoplasm. In contrast, Vpr mutants E21, 24P, L64S, and L67S were inactive in cell cycle arrest and were localized in the cytoplasm (FIGS. 3A—3O). These results clearly indicate that the helical domain and amino acids in the carboxy terminal domain control the cell cycle arrest function of Vpr. In support of this, Vpr from HXB2 (18 amino acid deletion in C-terminus) does not induce either cell cycle arrest or morphological differentiation, and exhibits the diffused nuclear localization phenotype. These results support the importance of helical domains for the virion incorporation, nuclear localization and cell cycle arrest functions of Vpr. Importantly these Vpr mutants clearly segregate the nuclear localization and cell cycle arrest functions, as well as, morphological differentiation (Table 1).

Discussion

Figure 5:
FIG. 5 shows domains of Vpr required for virion incorporation, subcellular localization, and cell cycle arrest/differentiation. The amino acid sequence of macrophage trophic clone 89.6 Vpr is shown with the alpha-helical. LR and C-terminal domains indicated. Critical amino acid residues and domains essential for different functions of Vpr were determined by mutational analysis.
Figure 6A:
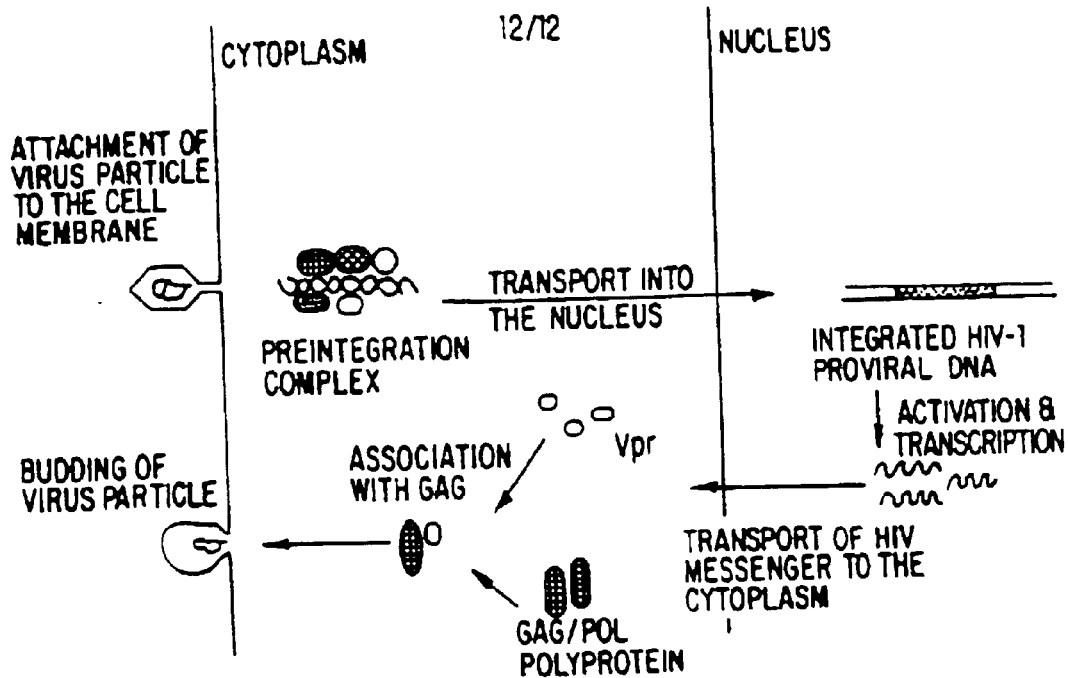
FIGS. 6A–6B shows a model for the different functions of HIV-1 Vpr.

Vpr is unique among the HIV-1 accessory, proteins because of its association with virus particles. Recently, we have shown that the protein encoded by the gag gene is sufficient for incorporation of Vpr into virus particles (FIG. 6A). The presence of Vpr in the virion is a strong indication that this protein may have a functional role early in viral replication. When expressed in the absence of other viral proteins, Vpr was shown to be localized in the nucleus and to arrest cells at G2/M phase of cell division (He, J. et al., *J. Virol.,* 1995, 69: 6705–6711). In order to define the interrelationship between the different functions (virion incorporation, nuclear localization, cell cycle arrest, and differentiation) of Vpr, we generated a number of molecules with mutations in different structural domains of Vpr. Our results clearly show that virion incorporation and nuclear localization of Vpr are controlled by putative helical domains and the leucine/isoleucine rich domain, while cell cycle arrest is largely controlled by C-terminal domain (amino acid 71 to 82) (FIG. 5). Most notable, however, was that incorporation experiments showed that proline substitution mutants were not incorporated into virus-like particles. The helix-destabilizing properties of prolines are well documented (Chou, P. Y. and G. D. Fasman., *Annu. Rev. Biochem.,* 1978, 47: 251–276: Tacke, E. et al., *Virology,* 1993, 197: 274–282.). Substitution of proline for glutamic acid 21, 24 (E21, 24P) and alanine 59 (A59P) in the helical domains abrogated Vpr incorporation into virus like particles suggesting that putative helical domains are required for the virion incorporation of Vpr.

Mutations in alanine 30 (A30S and A30L, resulted in markedly reduced levels of Vpr incorporation into virus-like particles. Furthermore, substitution of alanine for four leucines (α L-A) in the helical domain resulted in a Vpr mutant which was not incorporated into virus-like particles suggesting the importance of hydrophobic leucines in the helical domains for virion packaging. All the helical domain mutants except A30L showed impaired virion incorporation and nuclear localization. These impairments may be due to altered structural conformation and/or stability of the mutant Vpr proteins. An analysis of the protein helical motif, correlated with specific biological functions, suggests that amino acid residues in the helices are essential for normal processing and stability by ensuring proper conformation. In accordance with these observations, the putative helical domains present in Vpr play an important role in virion packaging into virus particles.

Figure 6B:
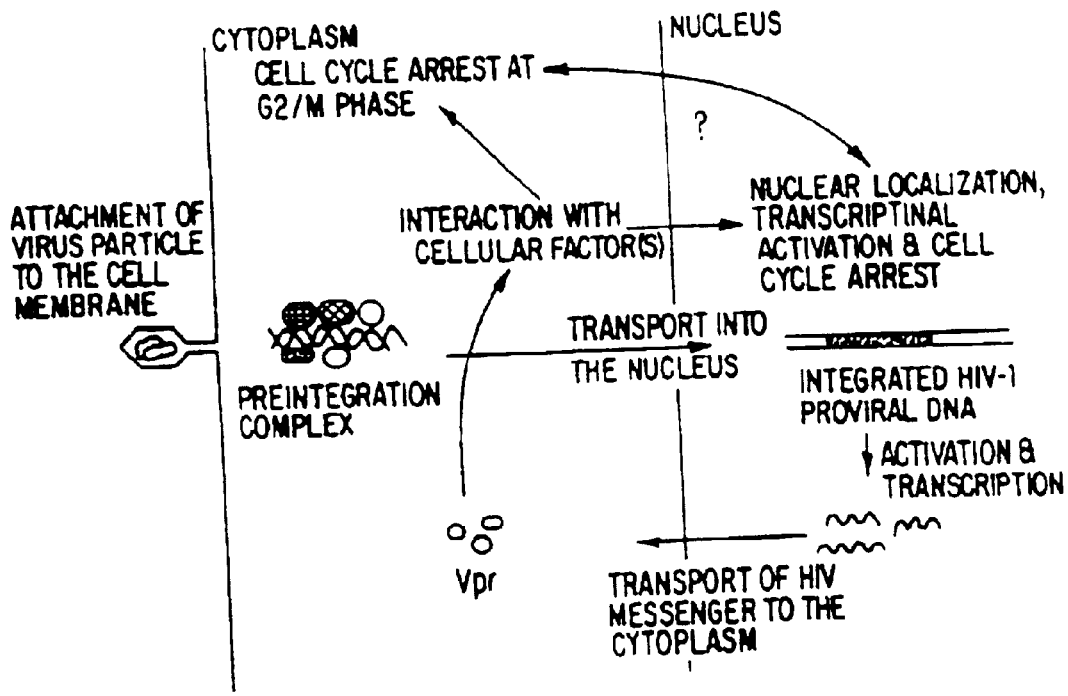

Immunofluorescence analysis clearly indicates that the putative helical and LR domains of Vpr play an important role in the transport of Vpr into the nucleus. The importance of helical domains for nuclear targeting is supported by the impairment of nuclear localization for substitution mutants E21, 24P and A59P which were shown to disrupt the conformation of the helical structure. In contrast, mutation in the hydrophobic face of the helix in Vpr (A30L) resulted in a mutant protein that retained the ability to localize in the nucleus but diminished the virion incorporation function of Vpr. Replacement of leucines by serine in the LR domain abrogated the nuclear localization but retained the virion packaging ability of Vpr. The mechanism by which Vpr is transported to the nucleus and the means by which these residues mediate these functions are unknown. The sequences identified for the nuclear localization of Vpr do not contain a canonical nuclear targeting motif which could be expected to be directly responsible for nuclear targeting. Helical structures are known to support protein-protein interactions, and thus it may be through association with cellular protein(s) that Vpr translocates to the nucleus (FIG. 6B). The recent observations from our laboratory and others suggest that Vpr can associate with cellular factor(s) is consistent with this hypothesis (Refaeli, Y. et al., *Proc. Natl. Acad. Sci. U.S.A.* 1995, 92: 3621–3625. Zhao, L-J. et al., *J. Biol. Chem.,* 1994. 269: 15577–15582). These factors include a putative glucocorticoid receptor complex which may be translocated to the nucleus with Vpr (FIG. 6B). Zhao et al., (*J. Biol. Chem* Supra) recently demonstrated that a mutation in LR domain. involved in the interaction with a cellular protein (RIP), abolishes the protein-protein interactions. RIP has been shown to be present in the cytoplasm and nucleus. It is possible that the translocation of Vpr into the nucleus may be related to its association with the RIP protein or protein complex. In contrast to the helical and LR domains, the conserved Gly75 and Cys76 in the C-terminus are dispensable for the nuclear translocation and virion incorporation properties of Vpr. These results suggest that Vpr nuclear translocation does not require a typical NLS. All the proteins are synthesized in the cytoplasm and some are transported to the nucleus through recognition of a specific NLS rich in basic amino acid residues. However, others are transported through piggyback binding to another protein which has a NLS (Dingwall, C. and R. A. Laskey, *Trends Biochem, Sci.,* 1991, 16: 478–481). It is also possible that nuclear transport of Vpr is not NLS dependent.

Interestingly, of all the Vpr mutant molecules, A30L and G75A retained the wild-type nuclear localization pattern but were impaired in the cell cycle arrest function. In contrast, Vpr mutants E21, 24P, αL-A, L64S, L67S, and L68S retain the ability to arrest the cell at G2/M phase but failed to localize in the nucleus. In addition, Vpr mutant A59P is impaired for all the functions of Vpr despite detectable expression. Presumably, Vpr blocks cell division by modifying a p34cdc2-Cyclin B protein complex which is involved in cell cycle regulation, Vpr mutants that fail to arrest the cell cycle are not likely to interact with a cellular factor involved in cell cycle regulation or may interact without triggering signals necessary for cell cycle arrest.

The importance of Vpr's ability to arrest the cell cycle and its direct relevance to HIV-1 replication in monocytes/macrophages or AIDS pathogenesis is under intensive investigation. Vpr may nonspecifically interfere with the complicated events of cell division. However, results from our and other laboratories suggest that this is not the case, since two Vpr mutants (A30L and G75A) localized in the nucleus but were not involved in cell cycle arrest function of Vpr. In contrast, Vpr mutant L68S localized in the cytoplasm and maintained the cell cycle arrest activity. Vpr is capable of importing a large preintegration complex into the nucleus of nondividing cells (Heinzinger, N. K. et al., *Proc. Natl. Acad. Sci. USA*. 1994, 91: 7311–7315). Results obtained from the putative helical and LR domain mutants clearly indicate that nuclear localization is not essential for the cell cycle arrest activity of Vpr. In this context Fletcher et al., (9*EMBO*, 1996, 15: 6155–6165.) reported that nuclear import of a preintegration complex and cell cycle arrest activities are mediated by two separate genes (Vpx and Vpr) in HIV-2/SIV. The identification of the amino acid residues of Vpr required for virion incorporation, nuclear localization, cell cycle arrest, as well as, host cell differentiation may have practical importance. Recently, lentiviruses have been suggested to have utility as gene therapy vectors due to their inherent unique property of nuclear import and genome integration in nondividing cells (Naldini, L. et al., *Science*, 1996, 272: 263–267.). The segregation of the nuclear import function of Vpr from the cell cycle arrest/differentiation function allow for construction of gene delivery vectors which take advantage of the nuclear import property of Vpr without other less desirable Vpr activities.

TABLE 1

Effect of mutagenesis on Vpr virion incorporation, subcellular localization and cell cycle arrest/differentiation functions

| Clone designation | Expression | Incorporation into virus-like particles | Subcellular localization | Cell cycle arrest | Differentiation |
|---|---|---|---|---|---|
| Vpr wt | + | + | nuc | + | + |
| E21-24P | + | − | cyto | − | − |
| αL-A | + | − | cyto | + | + |
| A30S | + | + | cyto > nuc | − | − |
| A30L | + | + | nuc | − | − |
| A59P | + | − | cyto | − | − |
| L64S | + | + | cyto > nuc | +/− | +/− |
| L67S | + | + | cyto | − | − |
| L68S | + | + | cyto | + | + |
| H71C | + | + | cyto > nuc | − | − |
| H71Y | + | +/− | cyto > nuc | − | − |
| G75A | + | + | nuc | +/− | +/− |
| C76S | + | + | cyto + nuc | +/− | +/− |
| Vpr(HXB2) | + | + | cyto + nuc | − | nd |

What is claimed is:

1. A conjugated composition comprising at least one a nuclear localization sequence fragment of HIV-1 Vpr protein (SEQ No: 1) consisting of amino acid sequence 17–36 and/or amino acid sequence 59–84 of said HIV-1 Vpr protein conjugated to a therapeutic compound, wherein said therapeutic compound is a nucleic acid molecule.

2. The conjugated composition of claim 1, wherein said nucleic acid molecule is a DNA vaccine plasmid conjugated to said fragment of HIV-1 Vpr protein by tonic bonds.

3. The conjugated composition of claim 1, wherein said nucleic acid molecule is an antisense molecule.

4. The conjugated composition of claim 1, wherein said nucleic acid molecule is an antisense oligonucleotide.

5. A method of delivering a therapeutic compound to the nucleus of a cell comprising the step of:

contacting said cell with a conjugated compound, wherein said conjugated compound comprises said therapeutic compound conjugated to at least one nuclear localization sequence fragment of HIV-1 Vpr protein (SEQ No: 1) consisting of amino acid sequence 17–36 and/or amino acid sequence 59–84 of said HIV-1 Vpr protein; wherein said therapeutic compound is a nucleic acid molecule, and wherein said conjugated compound is taken up by said cell and localized to the nucleus of said cell.

6. The method of claim 5, wherein said nucleic acid molecule is a DNA molecule.

7. The method of claim 5, wherein said nucleic acid molecule is a plasmid DNA molecule.

8. The method of claim 5, wherein said nucleic acid molecule is an antisense molecule.

9. The method of claim 5, wherein said nucleic acid molecule is an antisense oligonucleotide.

10. A conjugated composition comprising a nuclear localization sequence fragment of HIV-1 Vpr protein (SEQ No: 1) comprising amino acid sequence 17–36 and/or amino acid sequence 59–84 of said HIV-1 Vpr protein conjugated to a therapeutic compound, wherein said fragment of HIV-1 Vpr protein is less than 50 amino acids.

11. The conjugated composition of claim 10, wherein said fragment of HIV-1 Vpr protein further comprises a polycationic amino acid sequence.

12. The conjugated composition of claim 10, wherein said therapeutic compound is a DNA vaccine plasmid conjugated to said fragment of HIV-1 Vpr protein ionic bonds.

13. The conjugated composition of claim 10, wherein said fragment of HIV-1 Vpr protein further comprises a polycationic amino acid sequence and said therapeutic compound is a nucleic acid molecule conjugated to said polycationic amino acid sequence by ionic bonds.

14. The conjugated composition of claim 10, wherein said therapeutic compound is an antisense molecule.

15. The conjugated composition of claim 10, wherein said therapeutic compound is an antisense oligonucleotide.

16. A method of delivering a therapeutic compound to the nucleus of a cell comprising the step of:

contacting said cell with a conjugated compound, wherein said conjugated compound comprises said therapeutic compound conjugated to a nuclear localization sequence fragment of HIV-1 Vpr protein (SEQ No: 1) comprising amino acid sequence 17–36 and/or amino acid sequence 59–84 of said HIV-1 Vpr protein; wherein said fragment of HIV-1 Vpr protein is less than 50 amino acids, and wherein said conjugated compound is taken up by said cell and localized to the nucleus of said cell.

17. The method of claim 16, wherein said therapeutic compound is a DNA molecule.

18. The method of claim 16, wherein said therapeutic compound is a plasmid DNA molecule.

19. The method of claim 16, wherein said therapeutic compound is an antisense molecule.

20. The method of claim 16, wherein said therapeutic compound is an antisense oligonucleotide.

* * * * *

UNITED STATES PATENT AND TRADEMARK OFFICE
CERTIFICATE OF CORRECTION

PATENT NO. : 6,818,627 B1
DATED : November 16, 2004
INVENTOR(S) : Mahalingam et al.

It is certified that error appears in the above-identified patent and that said Letters Patent is hereby corrected as shown below:

Column 43,
Line 26, please delete "tonic" and insert -- ionic --.

Signed and Sealed this

Thirteenth Day of September, 2005

JON W. DUDAS
*Director of the United States Patent and Trademark Office*

SEQUENCE LISTING

<160> NUMBER OF SEQ ID NOS: 18

<210> SEQ ID NO 1
<211> LENGTH: 96
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 1

Met Gln Ala Pro Glu Asp Gln Gly Pro Gln Arg Glu Tyr Pro Asn
  1               5                  10                  15

Asp Trp Thr Leu Glu Leu Leu Glu Glu Leu Lys Asn Glu Ala Val Arg
                 20                  25                  30

His Phe Pro Arg Ile Trp Leu His Ser Leu Gly Gln His Ile Tyr Glu
             35                  40                  45

Thr Tyr Gly Asp Thr Trp Thr Gly Val Glu Ala Leu Ile Arg Ile Leu
         50                  55                  60

Gln Gln Leu Leu Phe Ile His Phe Arg Ile Gly Cys Arg His Ser Arg
 65                  70                  75                  80

Ile Gly Ile Ile Gln Gln Arg Arg Thr Arg Asn Gly Ala Ser Lys Ser
                     85                  90                  95

<210> SEQ ID NO 2
<211> LENGTH: 101
<212> TYPE: PRT
<213> ORGANISM: Artificial Sequence
<220> FEATURE:
<223> OTHER INFORMATION: Description of Artificial Sequence: Novel -continued Sequence

<400> SEQUENCE: 2

Met Glu Glu Arg Pro Pro Glu Asn Glu Gly Pro Gln Arg Glu Pro Trp
1               5                   10                  15

Asp Glu Trp Val Val Glu Val Leu Glu Glu Leu Lys Glu Glu Ala Leu
            20                  25                  30

Lys His Phe Asp Pro Arg Leu Leu Thr Ala Leu Gly Asn His Ile Tyr
        35                  40                  45

Asn Arg His Gly Asp Thr Leu Glu Gly Ala Gly Glu Leu Ile Arg Ile
    50                  55                  60

Leu Gln Arg Ala Leu Phe Met His Phe Arg Gly Gly Cys Ile His Ser
65                  70                  75                  80

Arg Ile Gly Gln Pro Gly Gly Gly Asn Pro Leu Ser Ala Ile Pro Pro
                85                  90                  95

Ser Arg Ser Met Leu
            100

<210> SEQ ID NO 3
<211> LENGTH: 111
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 3

Met Thr Asn Pro Arg Glu Thr Ile Pro Pro Gly Asn Ser Gly Glu Glu
1               5                   10                  15

Thr Ile Glu Glu Ala Phe Asp Trp Leu Asp Arg Thr Val Glu Ala Ile
            20                  25                  30

Asn Arg Glu Ala Val Asn His Leu Pro Arg Glu Leu Ile Phe Gln Val
        35                  40                  45

Trp Gln Arg Ser Trp Arg Tyr Trp His Asp Glu Gln Gly Met Ser Arg
    50                  55                  60

Ser Tyr Thr Lys Tyr Arg Tyr Leu Cys Leu Met Gln Lys Ala Val Phe
65                  70                  75                  80

Met His Phe Lys Lys Gly Cys Thr Cys Arg Gly Glu Gly His Gly Pro
                85                  90                  95

Gly Gly Trp Arg Ser Gly Pro Pro Pro Pro Pro Pro Gly Leu
            100                 105                 110

<210> SEQ ID NO 4
<211> LENGTH: 96
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 4

Met Glu Gln Ala Pro Glu Asp Gln Gly Pro Gln Arg Glu Pro Tyr Asn
1               5                   10                  15

Asp Trp Thr Leu Glu Leu Leu Glu Glu Leu Lys Asn Glu Ala Val Arg
            20                  25                  30

His Phe Pro Arg Ile Trp Leu His Ser Leu Gly Gln His Ile Tyr Glu
        35                  40                  45

Thr Tyr Gly Asp Thr Trp Thr Gly Val Glu Ala Leu Ile Arg Ile Leu
    50                  55                  60

```
Gln Gln Leu Leu Phe Ile His Phe Arg Ile Gly Cys Arg His Ser Arg
 65                  70                  75                  80

Ile Gly Ile Ile Gln His Arg Arg Thr Arg Asn Gly Ala Ser Lys Ser
                 85                  90                  95
```

<210> SEQ ID NO 5
<211> LENGTH: 96
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 5

```
Met Glu Gln Ala Pro Glu Asp Gln Gly Pro Gln Arg Glu Pro Tyr Asn
 1               5                  10                  15

Asp Trp Thr Leu Pro Leu Leu Pro Glu Leu Lys Asn Glu Ala Val Arg
                 20                  25                  30

His Phe Pro Arg Ile Trp Leu His Ser Leu Gly Gln His Ile Tyr Glu
                 35                  40                  45

Thr Tyr Gly Asp Thr Trp Thr Gly Val Glu Ala Leu Ile Arg Ile Leu
 50                  55                  60

Gln Gln Leu Leu Phe Ile His Phe Arg Ile Gly Cys Arg His Ser Arg
 65                  70                  75                  80

Ile Gly Ile Ile Gln His Arg Arg Thr Arg Asn Gly Ala Ser Lys Ser
                 85                  90                  95
```

<210> SEQ ID NO 6
<211> LENGTH: 96
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 6

```
Met Glu Gln Ala Pro Glu Asp Gln Gly Pro Gln Arg Glu Pro Tyr Asn
 1               5                  10                  15

Asp Trp Thr Ala Glu Ala Ala Glu Glu Ala Lys Asn Glu Ala Val Arg
                 20                  25                  30

His Phe Pro Arg Ile Trp Leu His Ser Leu Gly Gln His Ile Tyr Glu
                 35                  40                  45

Thr Tyr Gly Asp Thr Trp Thr Gly Val Glu Ala Leu Ile Arg Ile Leu
 50                  55                  60

Gln Gln Leu Leu Phe Ile His Phe Arg Ile Gly Cys Arg His Ser Arg
 65                  70                  75                  80

Ile Gly Ile Ile Gln His Arg Arg Thr Arg Asn Gly Ala Ser Lys Ser
                 85                  90                  95
```

<210> SEQ ID NO 7
<211> LENGTH: 96
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 7

```
Met Glu Gln Ala Pro Glu Asp Gln Gly Pro Gln Arg Glu Pro Tyr Asn
 1               5                  10                  15
```

-continued

```
Asp Trp Thr Leu Glu Leu Leu Glu Glu Leu Lys Asn Glu Ser Val Arg
         20                  25                  30

His Phe Pro Arg Ile Trp Leu His Ser Leu Gly Gln His Ile Tyr Glu
         35                  40                  45

Thr Tyr Gly Asp Thr Trp Thr Gly Val Glu Ala Leu Ile Arg Ile Leu
         50                  55                  60

Gln Gln Leu Leu Phe Ile His Phe Arg Ile Gly Cys Arg His Ser Arg
 65                  70                  75                  80

Ile Gly Ile Ile Gln His Arg Arg Thr Arg Asn Gly Ala Ser Lys Ser
                     85                  90                  95
```

<210> SEQ ID NO 8
<211> LENGTH: 96
<212> TYPE: PRT
<213> ORGANISM: Artificial Sequence
<220> FEATURE:
<223> OTHER INFORMATION: Description of Artificial Sequence: Novel Sequence

<400> SEQUENCE: 8

```
Met Glu Gln Ala Pro Glu Asp Gln Gly Pro Gln Arg Glu Pro Tyr Asn
 1               5                  10                  15

Asp Trp Thr Leu Glu Leu Leu Glu Glu Leu Lys Asn Glu Leu Val Arg
         20                  25                  30

His Phe Pro Arg Ile Trp Leu His Ser Leu Gly Gln His Ile Tyr Glu
         35                  40                  45

Thr Tyr Gly Asp Thr Trp Thr Gly Val Glu Ala Leu Ile Arg Ile Leu
         50                  55                  60

Gln Gln Leu Leu Phe Ile His Phe Arg Ile Gly Cys Arg His Ser Arg
 65                  70                  75                  80

Ile Gly Ile Ile Gln His Arg Arg Thr Arg Asn Gly Ala Ser Lys Ser
                     85                  90                  95
```

<210> SEQ ID NO 9
<211> LENGTH: 96
<212> TYPE: PRT
<213> ORGANISM: Artificial Sequence
<220> FEATURE:
<223> OTHER INFORMATION: Description of Artificial Sequence: Novel Sequence

<400> SEQUENCE: 9

```
Met Glu Gln Ala Pro Glu Asp Gln Gly Pro Gln Arg Glu Pro Tyr Asn
 1               5                  10                  15

Asp Trp Thr Leu Glu Leu Leu Glu Glu Leu Lys Asn Glu Ala Val Arg
         20                  25                  30

His Phe Pro Arg Ile Trp Leu His Ser Leu Gly Gln His Ile Tyr Glu
         35                  40                  45

Thr Tyr Gly Asp Thr Trp Thr Gly Val Glu Pro Leu Ile Arg Ile Leu
         50                  55                  60

Gln Gln Leu Leu Phe Ile His Phe Arg Ile Gly Cys Arg His Ser Arg
 65                  70                  75                  80

Ile Gly Ile Ile Gln His Arg Arg Thr Arg Asn Gly Ala Ser Lys Ser
                     85                  90                  95
```

<210> SEQ ID NO 10
<211> LENGTH: 96
<212> TYPE: PRT
<213> ORGANISM: Artificial Sequence
<220> FEATURE:

```
<223> OTHER INFORMATION: Description of Artificial Sequence: Novel
      Sequence

<400> SEQUENCE: 10

Met Glu Gln Ala Pro Glu Asp Gln Gly Pro Gln Arg Glu Pro Tyr Asn
 1               5                  10                  15

Asp Trp Thr Leu Glu Leu Leu Glu Glu Leu Lys Asn Glu Ala Val Arg
            20                  25                  30

His Phe Pro Arg Ile Trp Leu His Ser Leu Gly Gln His Ile Tyr Glu
        35                  40                  45

Thr Tyr Gly Asp Thr Trp Thr Gly Val Glu Ala Leu Ile Arg Ser Leu
    50                  55                  60

Gln Gln Leu Leu Phe Ile His Phe Arg Ile Gly Cys Arg His Ser Arg
65                  70                  75                  80

Ile Gly Ile Ile Gln His Arg Arg Thr Arg Asn Gly Ala Ser Lys Ser
                85                  90                  95

<210> SEQ ID NO 11
<211> LENGTH: 96
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 11

Met Glu Gln Ala Pro Glu Asp Gln Gly Pro Gln Arg Glu Pro Tyr Asn
 1               5                  10                  15

Asp Trp Thr Leu Glu Leu Leu Glu Glu Leu Lys Asn Glu Ala Val Arg
            20                  25                  30

His Phe Pro Arg Ile Trp Leu His Ser Leu Gly Gln His Ile Tyr Glu
        35                  40                  45

Thr Tyr Gly Asp Thr Trp Thr Gly Val Glu Ala Leu Ile Arg Ile Leu
    50                  55                  60

Gln Gln Ser Leu Phe Ile His Phe Arg Ile Gly Cys Arg His Ser Arg
65                  70                  75                  80

Ile Gly Ile Ile Gln His Arg Arg Thr Arg Asn Gly Ala Ser Lys Ser
                85                  90                  95

<210> SEQ ID NO 12
<211> LENGTH: 96
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 12

Met Glu Gln Ala Pro Glu Asp Gln Gly Pro Gln Arg Glu Pro Tyr Asn
 1               5                  10                  15

Asp Trp Thr Leu Glu Leu Leu Glu Glu Leu Lys Asn Glu Ala Val Arg
            20                  25                  30

His Phe Pro Arg Ile Trp Leu His Ser Leu Gly Gln His Ile Tyr Glu
        35                  40                  45

Thr Tyr Gly Asp Thr Trp Thr Gly Val Glu Ala Leu Ile Arg Ile Leu
    50                  55                  60

Gln Gln Leu Ser Phe Ile His Phe Arg Ile Gly Cys Arg His Ser Arg
65                  70                  75                  80

Ile Gly Ile Ile Gln His Arg Arg Thr Arg Asn Gly Ala Ser Lys Ser
```

85                  90                  95

<210> SEQ ID NO 13
<211> LENGTH: 96
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 13

Met Glu Gln Ala Pro Glu Asp Gln Gly Pro Gln Arg Glu Pro Tyr Asn
 1               5                  10                  15

Asp Trp Thr Leu Glu Leu Leu Glu Glu Leu Lys Asn Glu Ala Val Arg
                20                  25                  30

His Phe Pro Arg Ile Trp Leu His Ser Leu Gly Gln His Ile Tyr Glu
            35                  40                  45

Thr Tyr Gly Asp Thr Trp Thr Gly Val Glu Ala Leu Ile Arg Ile Leu
        50                  55                  60

Gln Gln Leu Leu Phe Ile Cys Phe Arg Ile Gly Cys Arg His Ser Arg
 65                  70                  75                  80

Ile Gly Ile Ile Gln His Arg Arg Thr Arg Asn Gly Ala Ser Lys Ser
                85                  90                  95

<210> SEQ ID NO 14
<211> LENGTH: 96
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 14

Met Glu Gln Ala Pro Glu Asp Gln Gly Pro Gln Arg Glu Pro Tyr Asn
 1               5                  10                  15

Asp Trp Thr Leu Glu Leu Leu Glu Glu Leu Lys Asn Glu Ala Val Arg
                20                  25                  30

His Phe Pro Arg Ile Trp Leu His Ser Leu Gly Gln His Ile Tyr Glu
            35                  40                  45

Thr Tyr Gly Asp Thr Trp Thr Gly Val Glu Ala Leu Ile Arg Ile Leu
        50                  55                  60

Gln Gln Leu Leu Phe Ile Tyr Phe Arg Ile Gly Cys Arg His Ser Arg
 65                  70                  75                  80

Ile Gly Ile Ile Gln His Arg Arg Thr Arg Asn Gly Ala Ser Lys Ser
                85                  90                  95

<210> SEQ ID NO 15
<211> LENGTH: 96
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 15

Met Glu Gln Ala Pro Glu Asp Gln Gly Pro Gln Arg Glu Pro Tyr Asn
 1               5                  10                  15

Asp Trp Thr Leu Glu Leu Leu Glu Glu Leu Lys Asn Glu Ala Val Arg
                20                  25                  30

His Phe Pro Arg Ile Trp Leu His Ser Leu Gly Gln His Ile Tyr Glu
            35                  40                  45

```
Thr Tyr Gly Asp Thr Trp Thr Gly Val Glu Ala Leu Ile Arg Ile Leu
         50                  55                  60

Gln Gln Leu Leu Phe Ile His Phe Arg Ile Ala Cys Arg His Ser Arg
 65                  70                  75                  80

Ile Gly Ile Ile Gln His Arg Arg Thr Arg Asn Gly Ala Ser Lys Ser
                 85                  90                  95

<210> SEQ ID NO 16
<211> LENGTH: 96
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 16

Met Glu Gln Ala Pro Glu Asp Gln Gly Pro Gln Arg Glu Pro Tyr Asn
  1               5                  10                  15

Asp Trp Thr Leu Glu Leu Leu Glu Glu Leu Lys Asn Glu Ala Val Arg
                 20                  25                  30

His Phe Pro Arg Ile Trp Leu His Ser Leu Gly Gln His Ile Tyr Glu
             35                  40                  45

Thr Tyr Gly Asp Thr Trp Thr Gly Val Glu Ala Leu Ile Arg Ile Leu
         50                  55                  60

Gln Gln Leu Leu Phe Ile His Phe Arg Ile Gly Ser Arg His Ser Arg
 65                  70                  75                  80

Ile Gly Ile Ile Gln His Arg Arg Thr Arg Asn Gly Ala Ser Lys Ser
                 85                  90                  95

<210> SEQ ID NO 17
<211> LENGTH: 78
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 17

Met Glu Gln Ala Pro Glu Asp Gln Gly Pro Gln Arg Glu Pro Tyr Asn
  1               5                  10                  15

Asp Trp Thr Leu Glu Leu Leu Glu Glu Leu Lys Asn Glu Ala Val Arg
                 20                  25                  30

His Phe Pro Arg Ile Trp Leu His Ser Leu Gly Gln His Ile Tyr Glu
             35                  40                  45

Thr Tyr Gly Asp Ile Trp Ile Gly Val Glu Ala Leu Ile Arg Ile Leu
         50                  55                  60

Gln Gln Leu Leu Phe Ile His Phe Gln Asn Trp Val Ser Thr
 65                  70                  75

<210> SEQ ID NO 18
<211> LENGTH: 96
<212> TYPE: PRT
<213> ORGANISM: Artificial Sequence
<220> FEATURE:
<223> OTHER INFORMATION: Description of Artificial Sequence: Novel
      Sequence

<400> SEQUENCE: 18

Met Glu Gln Ala Pro Glu Asp Gln Gly Pro Gln Arg Glu Tyr Pro Asn
  1               5                  10                  15
```

```
                                 -continued

Asp Trp Thr Leu Glu Leu Leu Glu Glu Leu Lys Asn Glu Ala Val Arg
            20              25                  30

His Phe Pro Arg Ile Trp Leu His Ser Leu Gly Gln His Ile Tyr Glu
            35              40                  45

Thr Tyr Gly Asp Thr Trp Thr Gly Val Glu Ala Leu Ile Arg Ile Leu
     50              55                  60

Gln Gln Leu Leu Phe Ile His Phe Arg Ile Gly Cys Arg His Ser Arg
 65              70              75                          80

Ile Gly Ile Ile Gln Gln Arg Arg Thr Arg Asn Gly Ala Ser Lys Ser
             85              90                      95
```